United States Patent [19]
Mahurkar

[11] Patent Number: 5,374,245
[45] Date of Patent: * Dec. 20, 1994

[54] REINFORCED MULTIPLE-LUMEN CATHETER AND APPARATUS AND METHOD FOR MAKING THE SAME

[76] Inventor: Sakharam D. Mahurkar, 6171 N. Sheridan Rd., #1112, Chicago, Ill. 60660

[*] Notice: The portion of the term of this patent subsequent to Jun. 22, 2010 has been disclaimed.

[21] Appl. No.: 55,830

[22] Filed: Apr. 28, 1993

Related U.S. Application Data

[63] Continuation-in-part of Ser. No. 776,873, Oct. 16, 1991, Pat. No. 5,221,244, which is a continuation of Ser. No. 463,285, Jan. 10, 1990, abandoned, and a continuation-in-part of Ser. No. 903,896, Jun. 25, 1992, abandoned.

[51] Int. Cl.$^5$ ............................................ A61M 25/00
[52] U.S. Cl. ...................................... 604/43; 604/281
[58] Field of Search ................................. 604/43–45, 604/264, 280, 281, 282

[56] References Cited

U.S. PATENT DOCUMENTS

| | | |
|---|---|---|
| Re. 31,873 | 4/1985 | Howes . |
| D. 250,349 | 11/1978 | McFarlane . |
| D. 254,444 | 3/1980 | Levine . |
| D. 256,617 | 8/1980 | Clemens . |
| D. 272,651 | 2/1984 | Mahurkar . |
| 256,590 | 4/1882 | Pfarre . |
| 390,177 | 9/1883 | Lee . |
| 433,636 | 6/1982 | Leeke et al. . |
| 701,075 | 5/1902 | McCully . |
| 998,339 | 7/1911 | Hollins . |
| 1,045,326 | 11/1912 | Ruflin . |
| 1,093,538 | 4/1914 | Clough . |
| 1,290,647 | 1/1919 | Nyvall . |
| 1,922,084 | 8/1933 | Gerow . |
| 2,175,726 | 10/1939 | Gebauer . |
| 2,230,218 | 2/1941 | Asche . |
| 2,234,961 | 3/1941 | Canada . |
| 2,268,321 | 12/1941 | Flynn ............................. 604/282 |
| 2,409,343 | 10/1946 | Curtis . |

(List continued on next page.)

FOREIGN PATENT DOCUMENTS

| | | |
|---|---|---|
| 834211 | 2/1976 | Belgium . |
| 1092927 | 1/1981 | Canada . |
| 50089 | 8/1982 | Canada . |
| 1150122 | 7/1983 | Canada . |
| 1193508 | of 1984 | Canada . |
| 1167727 | 5/1984 | Canada . |

(List continued on next page.)

OTHER PUBLICATIONS

Dow Corning, *Fabricating With Silastic Silicone Rubber,* ©*1990*.
McIntosh et al., "Double Lumen Catheter," J.A.M.A., Feb. 21, 1959 pp. 137/835–138/836.
Dorland's Illustrated Medical Dictionary, 25th Ed., W.
(List continued on next page.)

Primary Examiner—Ralph A. Lewis
Attorney, Agent, or Firm—Arnold, White & Durkee

[57] ABSTRACT

A method of making a multiple-lumen catheter using a co-extrusion die comprises the step of forming an elongated cylindrical tube made of silicone and having an internal septum extending along the length thereof to form at least a pair of longitudinal lumens. While the elongated cylindrical tube is being formed, a nylon reinforcing strip is arranged inside the tube such that the strip extends along the length of the tube. The tube is solidified and cut into individual multiple-lumen catheters. The nylon strip includes a pair of orthogonal side plates which aid in anchoring the nylon strip within the solidified tube.

An apparatus for making the multiple-lumen catheter comprises a co-extrusion die, a silicon extruder for injecting silicone into the die, and a pair of rollers for feeding a nylon strip into the die. The co-extrusion die has a circular opening containing a pair of mandrels extending within the die for a predetermined length, the mandrels being arranged substantially parallel to each other with a gap therebetween. The rollers feed the nylon strip into the gap between the mandrels while the extruder is injecting the silicone into the die.

19 Claims, 17 Drawing Sheets

U.S. PATENT DOCUMENTS

| | | |
|---|---|---|
| 2,473,742 | 6/1949 | Auzin . |
| 2,474,665 | 6/1949 | Guarino . |
| 2,564,977 | 8/1951 | Hu . |
| 2,590,895 | 4/1952 | Scarpellino . |
| 2,625,932 | 1/1953 | Salisbury . |
| 2,716,983 | 9/1955 | Windischman et al. . |
| 2,819,718 | 1/1958 | Goldman . |
| 2,930,378 | 3/1960 | Buyers . |
| 2,936,761 | 5/1960 | Snyder . |
| 3,042,045 | 7/1962 | Sheridan . |
| 3,175,554 | 3/1965 | Stewart . |
| 3,314,430 | 4/1967 | Alley et al. . |
| 3,324,853 | 6/1967 | Czorny et al. . |
| 3,324,854 | 6/1967 | Weese . |
| 3,331,371 | 7/1967 | Rocchi et al. . |
| 3,359,974 | 12/1967 | Khalil . |
| 3,394,705 | 7/1968 | Abramson . |
| 3,435,826 | 1/1969 | Fogarty . |
| 3,437,088 | 4/1969 | Bielinski . |
| 3,448,739 | 6/1969 | Stark et al. . |
| 3,452,756 | 7/1969 | Harautuneian . |
| 3,459,188 | 7/1965 | Roberts . |
| 3,463,152 | 8/1969 | Sorenson . |
| 3,467,101 | 9/1969 | Fogarty et al. . |
| 3,485,234 | 12/1969 | Stevens . |
| 3,490,973 | 1/1970 | Graff et al. . |
| 3,543,758 | 12/1970 | McWhorter . |
| 3,543,759 | 12/1970 | McWhorter . |
| 3,550,591 | 12/1970 | MacGregor . |
| 3,556,161 | 1/1971 | Roberts . |
| 3,566,874 | 3/1971 | Sheperd et al. . |
| 3,593,713 | 7/1971 | Bogoff et al. . |
| 3,599,620 | 8/1971 | Balin . |
| 3,612,050 | 9/1971 | Sheridan . |
| 3,634,924 | 1/1972 | Blake et al. . |
| 3,683,908 | 8/1972 | Michael et al. . |
| 3,726,281 | 4/1973 | Norton et al. . |
| 3,746,003 | 7/1973 | Blake et al. . |
| 3,756,234 | 9/1973 | Kopp . |
| 3,771,527 | 11/1973 | Ruisi . |
| 3,774,605 | 11/1973 | Jewett . |
| 3,799,172 | 3/1974 | Szpur . |
| 3,804,097 | 4/1974 | Rudie . |
| 3,823,720 | 7/1974 | Tribble . |
| 3,828,767 | 8/1974 | Spiroff . |
| 3,830,234 | 8/1974 | Kopp . |
| 3,848,602 | 11/1974 | Gutnick . |
| 3,875,938 | 4/1975 | Mellor . |
| 3,885,567 | 5/1975 | Ross . |
| 3,896,815 | 7/1975 | Fettel et al. . |
| 3,978,863 | 9/1976 | Fettel et al. . |
| 3,995,623 | 12/1976 | Blake et al. . |
| 4,004,588 | 1/1977 | Alexander . |
| 4,016,879 | 4/1977 | Mellor . |
| 4,027,668 | 6/1977 | Dunn . |
| 4,037,599 | 7/1977 | Raulerson . |
| 4,057,065 | 11/1977 | Thow . |
| 4,072,146 | 2/1978 | Howes . |
| 4,096,860 | 6/1978 | McLaughlin . |
| 4,098,275 | 6/1978 | Consalvo . |
| 4,099,528 | 7/1978 | Sorenson et al. . |
| 4,100,246 | 7/1978 | Frisch . |
| 4,116,068 | 9/1978 | Megahed . |
| 4,134,402 | 1/1979 | Mahurkar . |
| 4,138,457 | 2/1979 | Rudd et al. ............................ 264/173 |
| 4,144,884 | 3/1979 | Tersteegen et al. . |
| 4,168,703 | 9/1979 | Kenigsberg . |
| 4,180,068 | 12/1979 | Jacobsen et al. . |
| 4,180,076 | 12/1979 | Betancourt . |
| 4,182,582 | 1/1980 | Youval et al. . |
| 4,202,332 | 5/1980 | Tersteegen et al. . |
| 4,203,436 | 5/1980 | Grimsrud . |
| 4,217,895 | 8/1980 | Sagae et al. . |
| 4,245,383 | 1/1981 | Boggs . |
| 4,257,416 | 3/1981 | Prager . |
| 4,270,535 | 7/1981 | Bogue et al. . |

(List continued on next page.)

FOREIGN PATENT DOCUMENTS

| | | |
|---|---|---|
| 36642 | 9/1981 | European Pat. Off. . |
| 0079719 | 11/1982 | European Pat. Off. . |
| 79719 | 5/1983 | European Pat. Off. . |
| 333308 | 2/1989 | European Pat. Off. . |
| 322225 | 6/1989 | European Pat. Off. . |
| 592193 | 4/1925 | France . |
| 1285953 | 7/1962 | France . |
| 1508959 | 1/1968 | France . |
| 2285148 | 4/1976 | France . |
| 2297640 | 8/1976 | France . |
| 821344 | 4/1982 | France . |
| 2530958 | 2/1984 | France . |
| 935625 | 11/1955 | Germany . |

(List continued on next page.)

OTHER PUBLICATIONS

B. Saunders Co., Philadelphia, 1974, p. 274.

Tsuchida et al., "Single Two–Lumen Cannula Dialysis", Toboku Journal Exp. Med., 1974, pp. 114, 159–101.

Tsuchida et al., "Design of a Two–Lumen–Piercing Needle That is Capable of Carrying Out Dialysis By Single Puncture", Journal of The Urological Society of Japan, vol. 65 (12), 1974, pp. 805–807.

Brenner & Rector, The Kidney, vol. III, W. B. Saunders Co., Philadelphia, 1976, p. 164.

(List continued on next page.)

U.S. PATENT DOCUMENTS

| | | |
|---|---|---|
| 4,314,555 | 2/1982 | Sagae . |
| 4,385,631 | 5/1983 | Uthmann . |
| 4,403,983 | 3/1983 | Edelman et al. . |
| 4,403,985 | 9/1983 | Boretos . |
| 4,406,656 | 9/1983 | Hattler et al. . |
| 4,419,095 | 12/1983 | Nerbergall et al. . |
| 4,443,333 | 4/1984 | Mahurkar . |
| 4,451,252 | 5/1984 | Martin . |
| 4,452,473 | 6/1984 | Ruschke . |
| 4,462,778 | 7/1984 | Calcagni ............ 264/173 |
| 4,473,369 | 9/1984 | Lueders et al. . |
| 4,484,585 | 11/1984 | Baier . |
| 4,493,696 | 5/1985 | Uldell . |
| 4,535,770 | 8/1985 | Lemole . |
| 4,543,087 | 9/1985 | Sommercorn et al. ........ 604/43 |
| 4,547,193 | 10/1985 | Rydell . |
| 4,568,329 | 2/1986 | Mahurkar . |
| 4,583,968 | 4/1986 | Mahurkar . |
| 4,592,749 | 6/1986 | Ebling et al. . |
| 4,617,433 | 10/1986 | Hoshikawa et al. . |
| 4,619,643 | 10/1986 | Bai ............ 604/43 |
| 4,623,327 | 11/1986 | Mahurkar . |
| 4,626,240 | 12/1986 | Edelman et al. . |
| 4,643,711 | 2/1987 | Bates . |
| 4,661,110 | 4/1987 | Fortier et al. . |
| 4,682,978 | 7/1987 | Martin ............ 604/43 |
| 4,684,363 | 8/1987 | Ari et al. . |
| 4,692,141 | 9/1987 | Mahurkar ............ 604/43 |
| 4,701,159 | 10/1987 | Brown et al. . |
| 4,723,948 | 2/1988 | Clark et al. . |
| 4,753,640 | 6/1988 | Nichols et al. . |
| 4,762,128 | 8/1988 | Rosenbluth . |
| 4,772,268 | 9/1988 | Bates . |
| 4,790,813 | 12/1988 | Kensey . |
| 4,795,439 | 1/1989 | Guest . |
| 4,827,921 | 5/1989 | Rugheimer . |
| 4,878,492 | 11/1989 | Sinofsky . |
| 4,894,057 | 1/1990 | Howes ............ 604/280 |
| 4,904,431 | 2/1990 | O'Maleki ............ 264/103 |
| 4,995,865 | 2/1990 | Gahara et al. . |
| 5,006,291 | 4/1991 | Fish ............ 264/103 |
| 5,063,018 | 11/1991 | Fontirroche et al. . |
| 5,075,062 | 12/1991 | Karpiel . |
| 5,135,599 | 8/1992 | Martin et al. ............ 604/43 |
| 5,221,255 | 6/1993 | Mahurkar et al. ............ 604/43 |
| 5,221,256 | 6/1993 | Mahurkar et al. ............ 604/43 |

FOREIGN PATENT DOCUMENTS

| | | |
|---|---|---|
| 2259865 | 6/1974 | Germany . |
| 3010841 | of 1980 | Germany . |
| 19346 | 6/1982 | Germany . |
| 55-88771 | 7/1980 | Japan . |
| 3427346 | 1/1986 | Netherlands . |
| 688450 | 3/1952 | United Kingdom . |
| 1419702 | 12/1975 | United Kingdom . |
| 1503469 | 10/1976 | United Kingdom . |
| 1006219 | 3/1983 | United Kingdom . |
| 1017315 | 5/1983 | U.S.S.R. . |
| 8404043 | 10/1984 | WIPO . |
| WO84/04664 | 12/1984 | WIPO . |

OTHER PUBLICATIONS

ASAIO Abstracts, vol. 5, 22nd Annual Meeting, San Francisco, Calif., Apr., 1–3, 1976, p. 164.

Kaplan et al., "A Co-Axial Dual Flow Catheter/Cannula For Single Puncture Dialysis", Dialysis & Transplantation, Dec./Jan. 1977, pp. 38–40, 42, 84.

"Terumo Cozxial Dual Flow Catheter", Terumo America, Inc. Apr., 1979 (two pages).

Reus et al. "Double–Lume Catheter in Extracorporeal Hemodialysis" Archives of Internal Medicine, vol. 113, Apr. 1964.

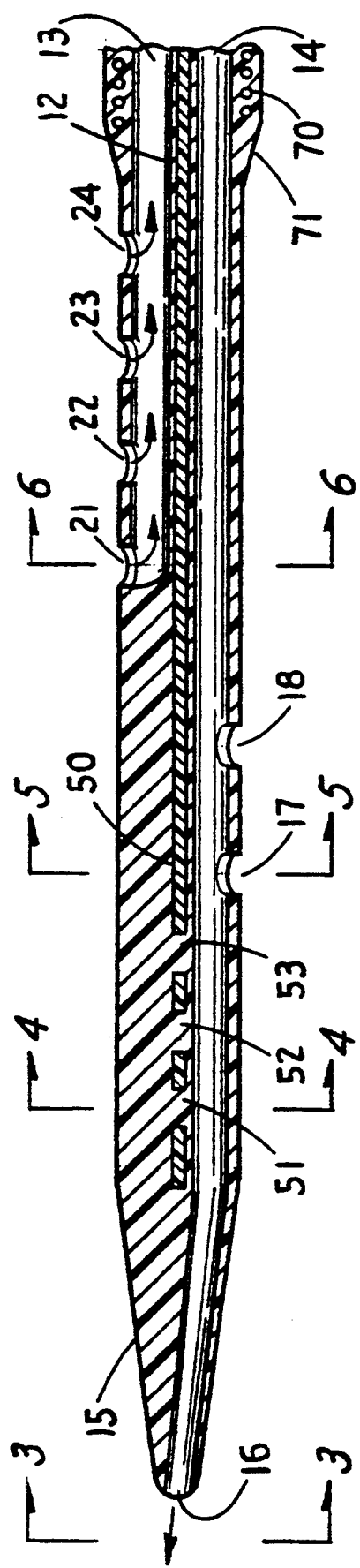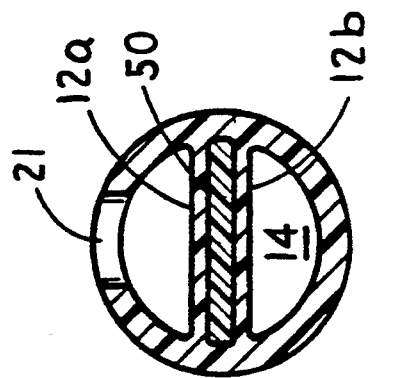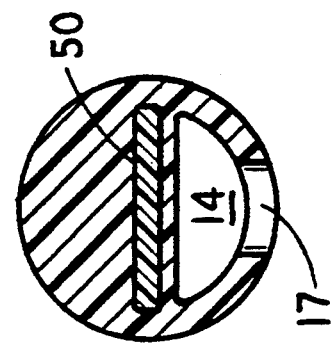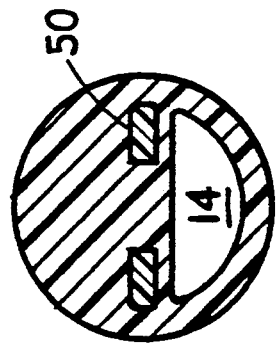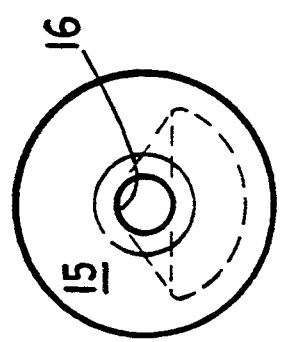

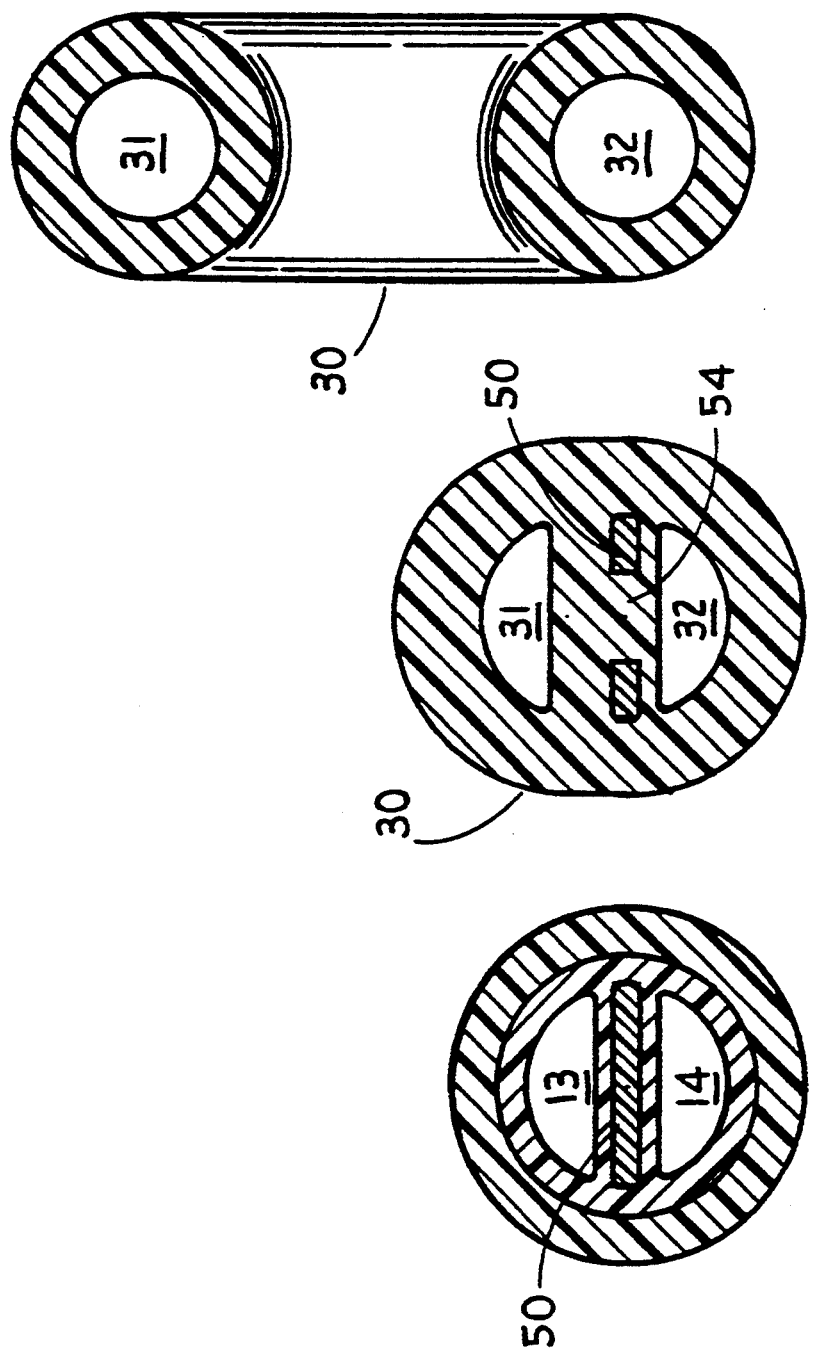

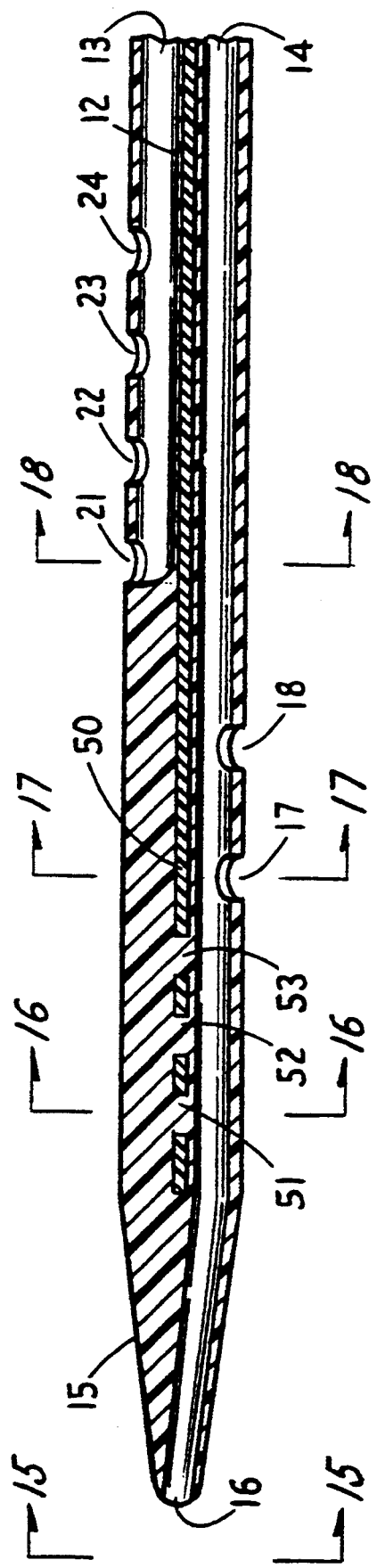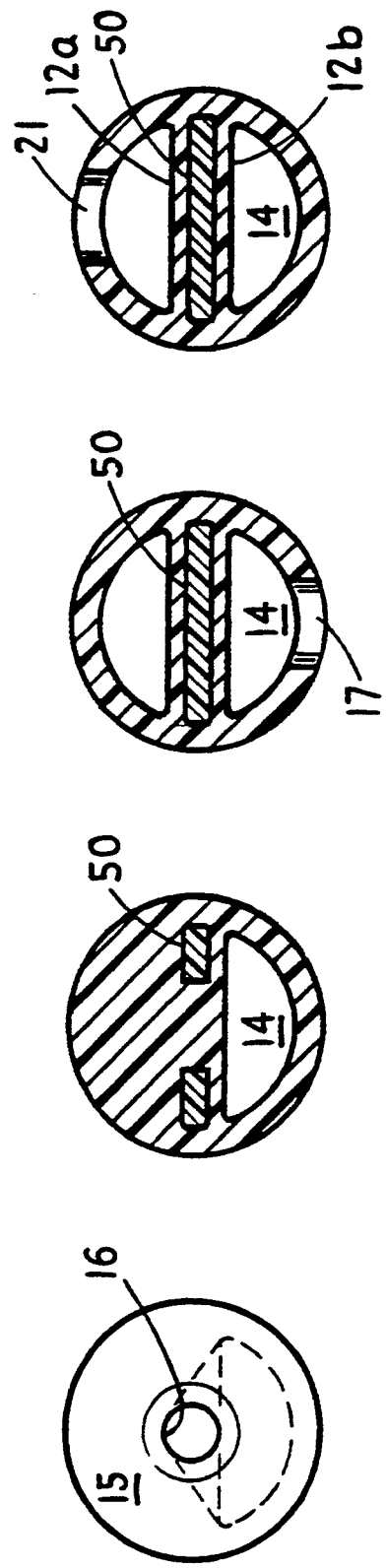

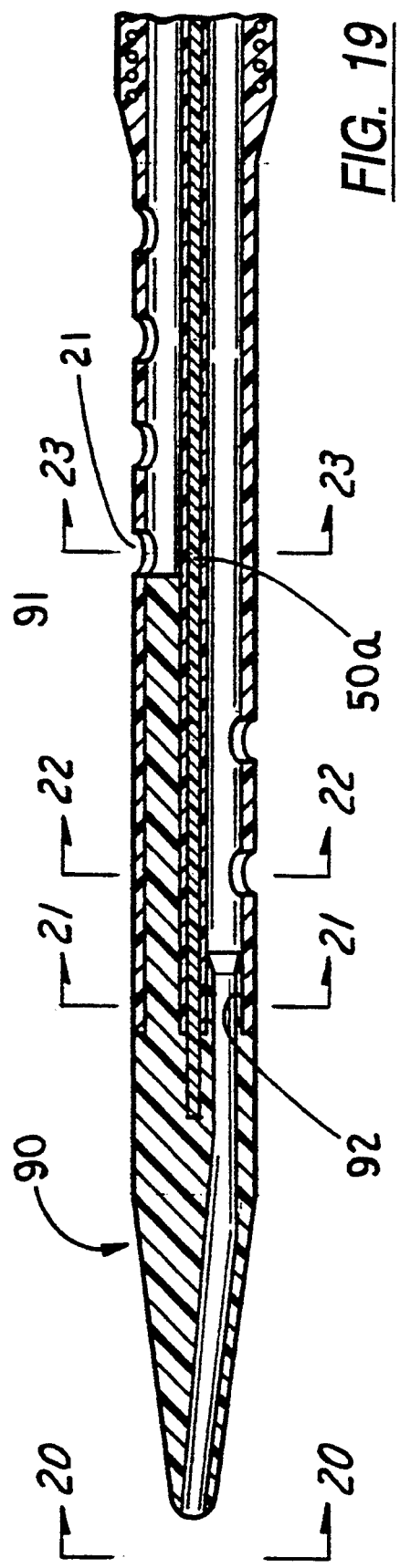
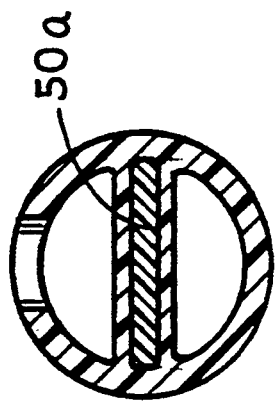
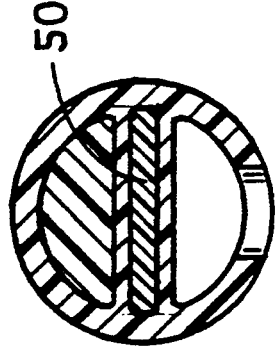
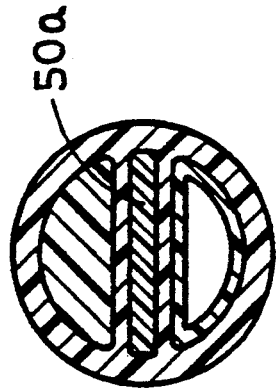
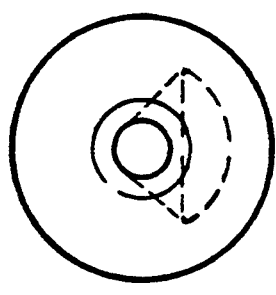

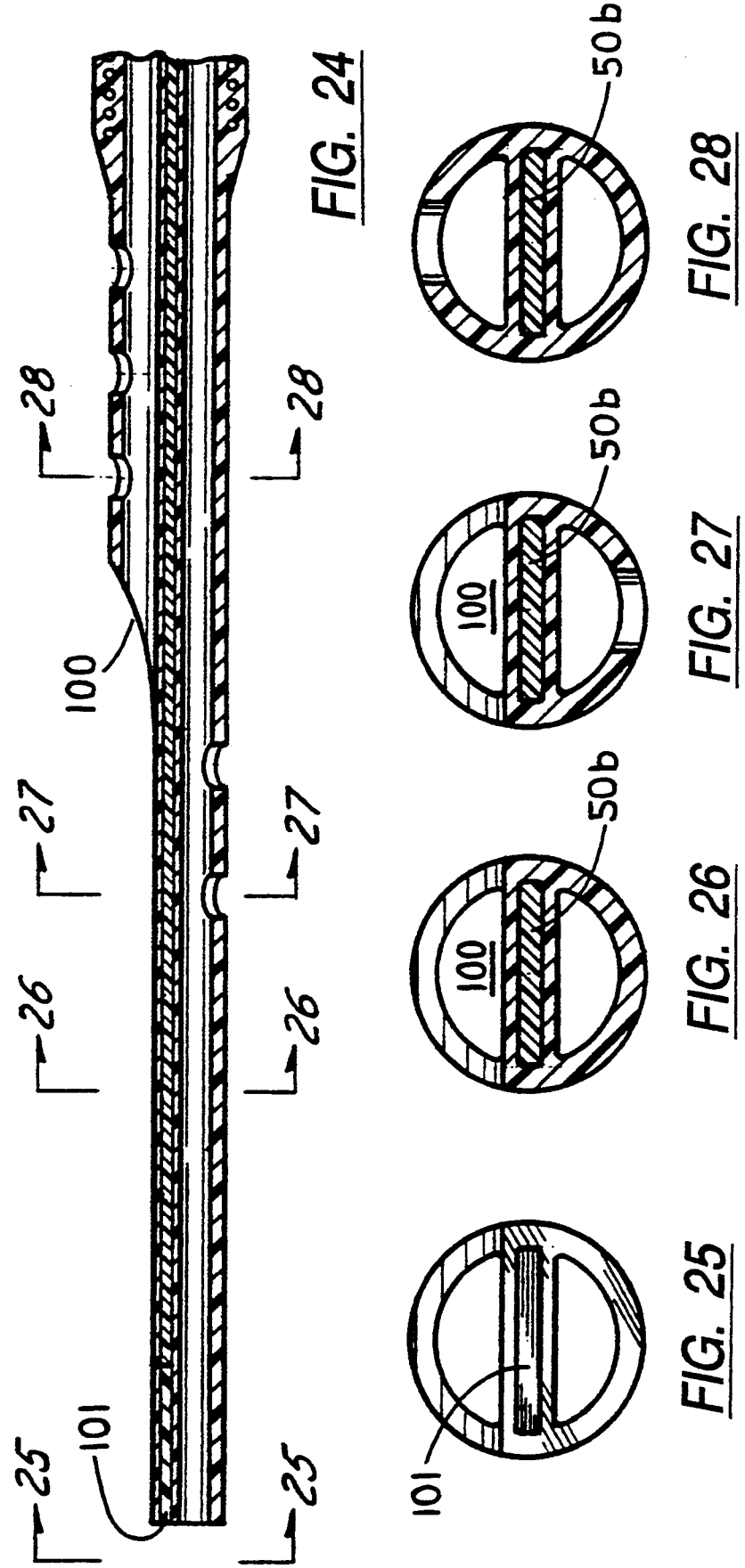

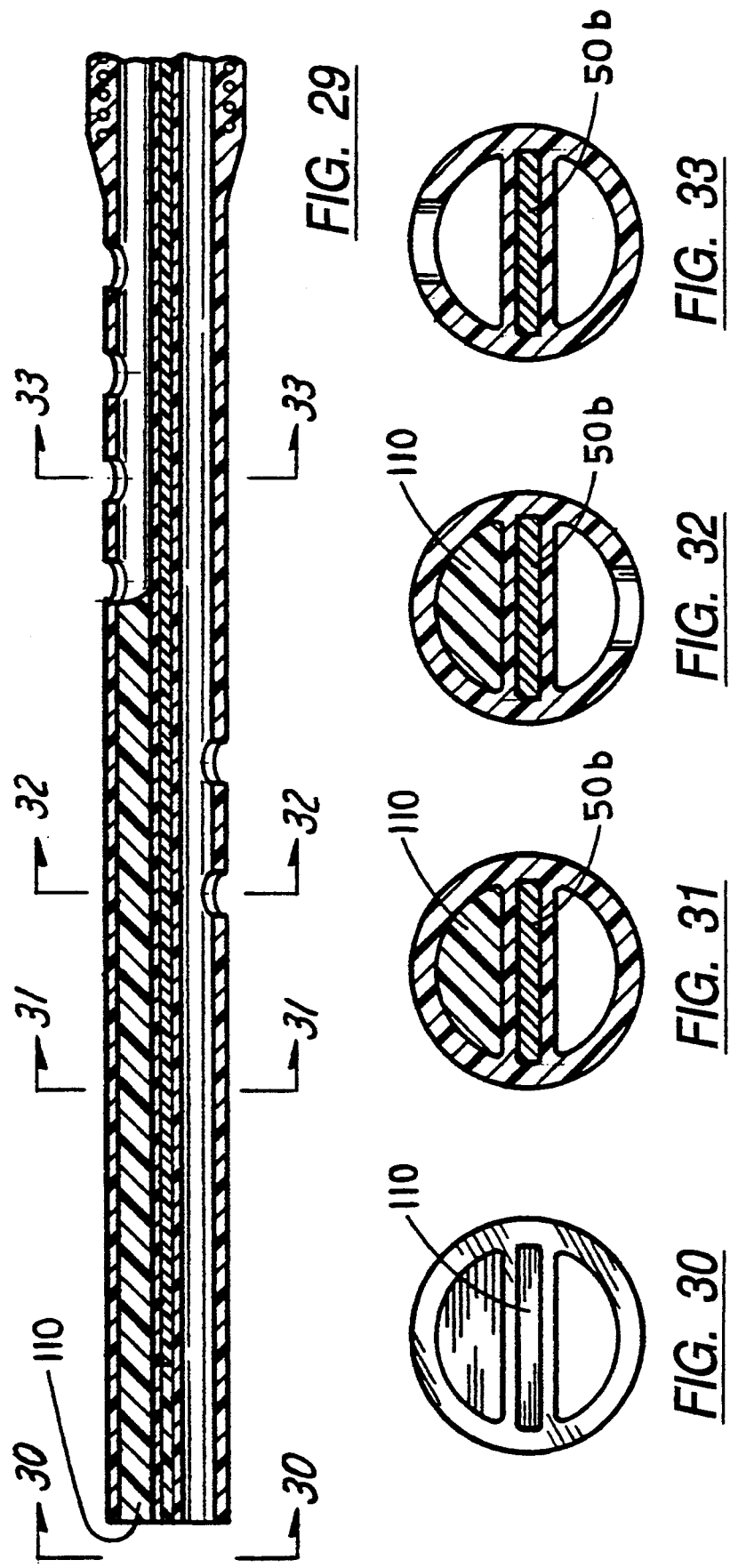

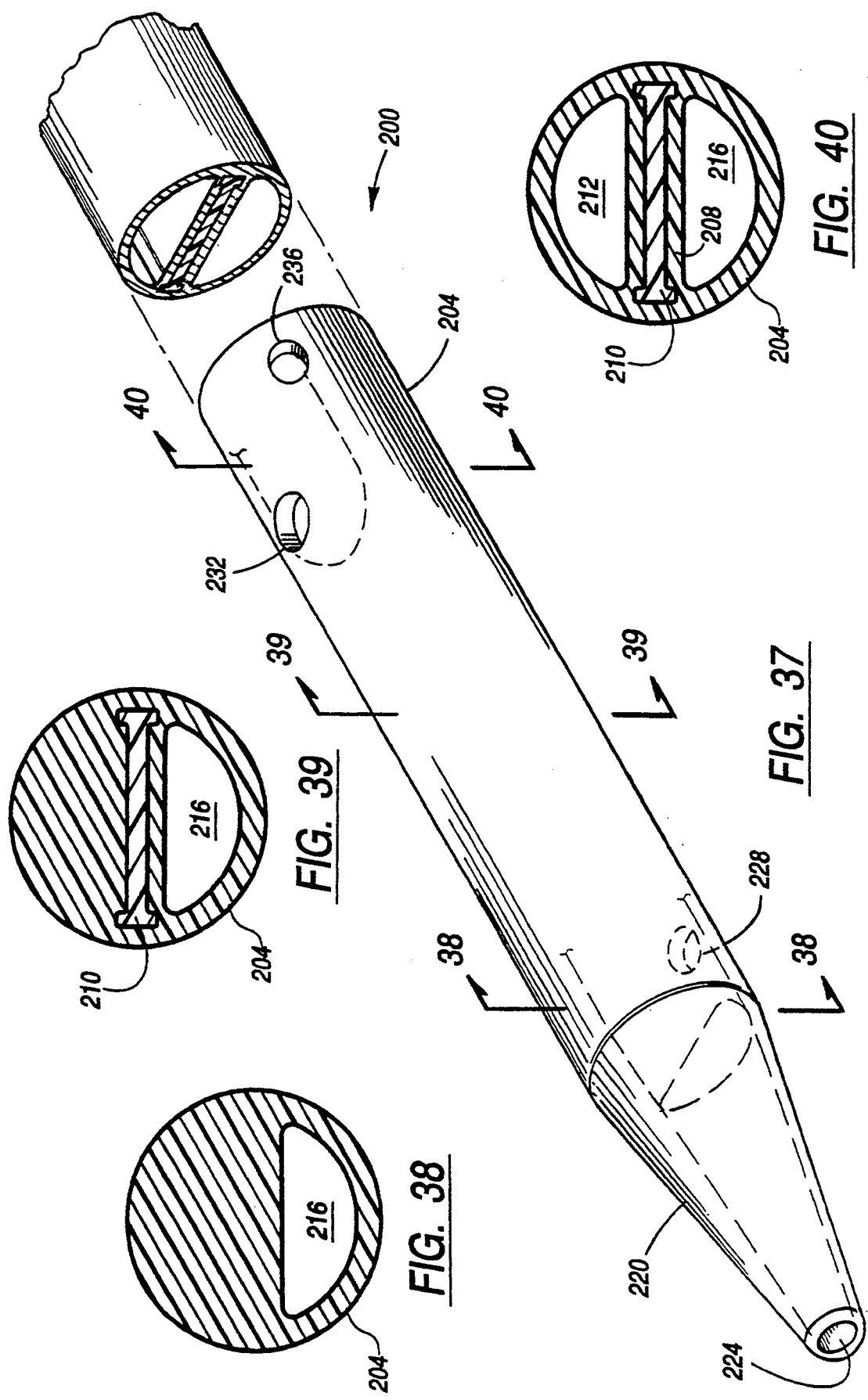

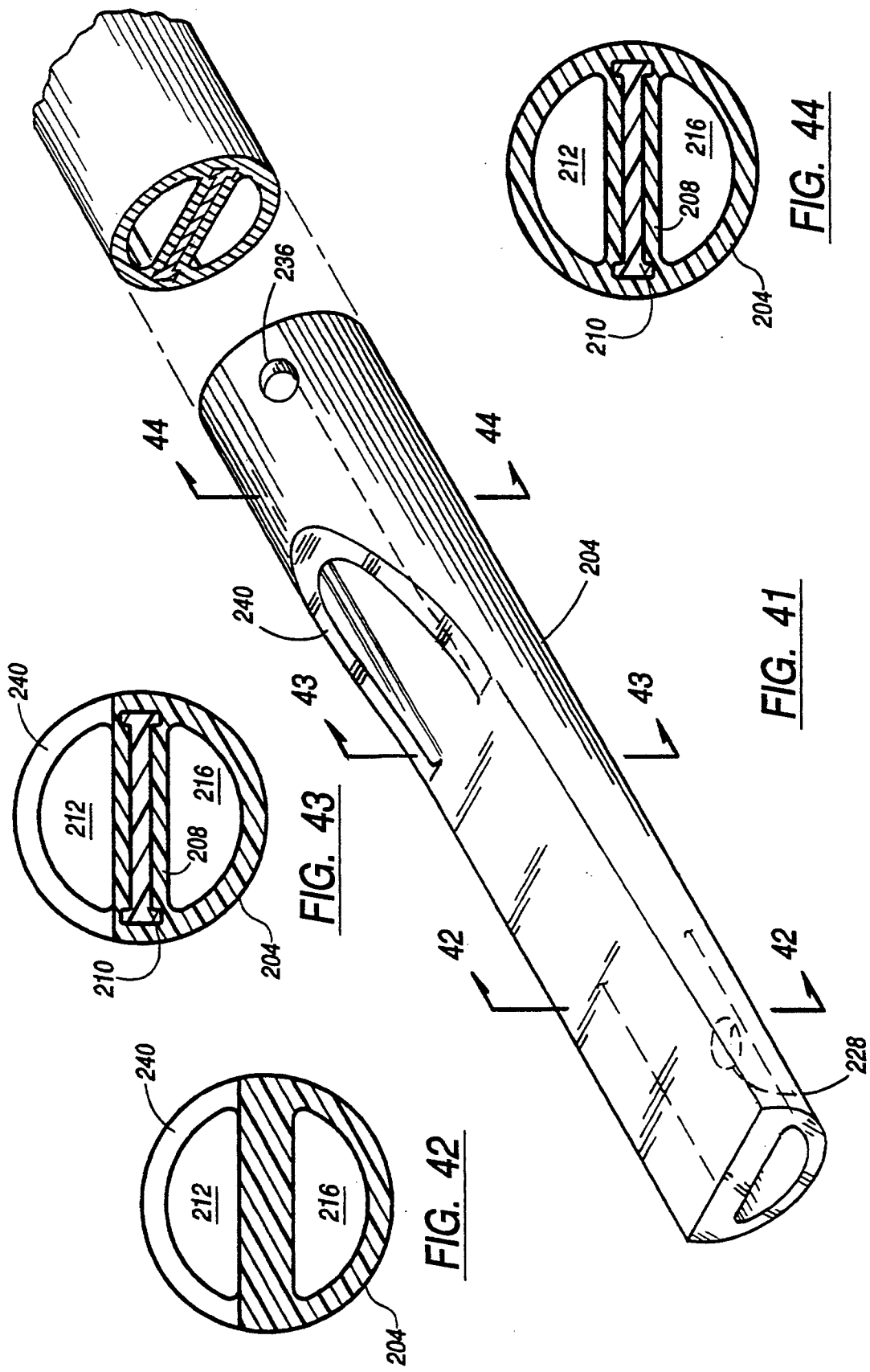

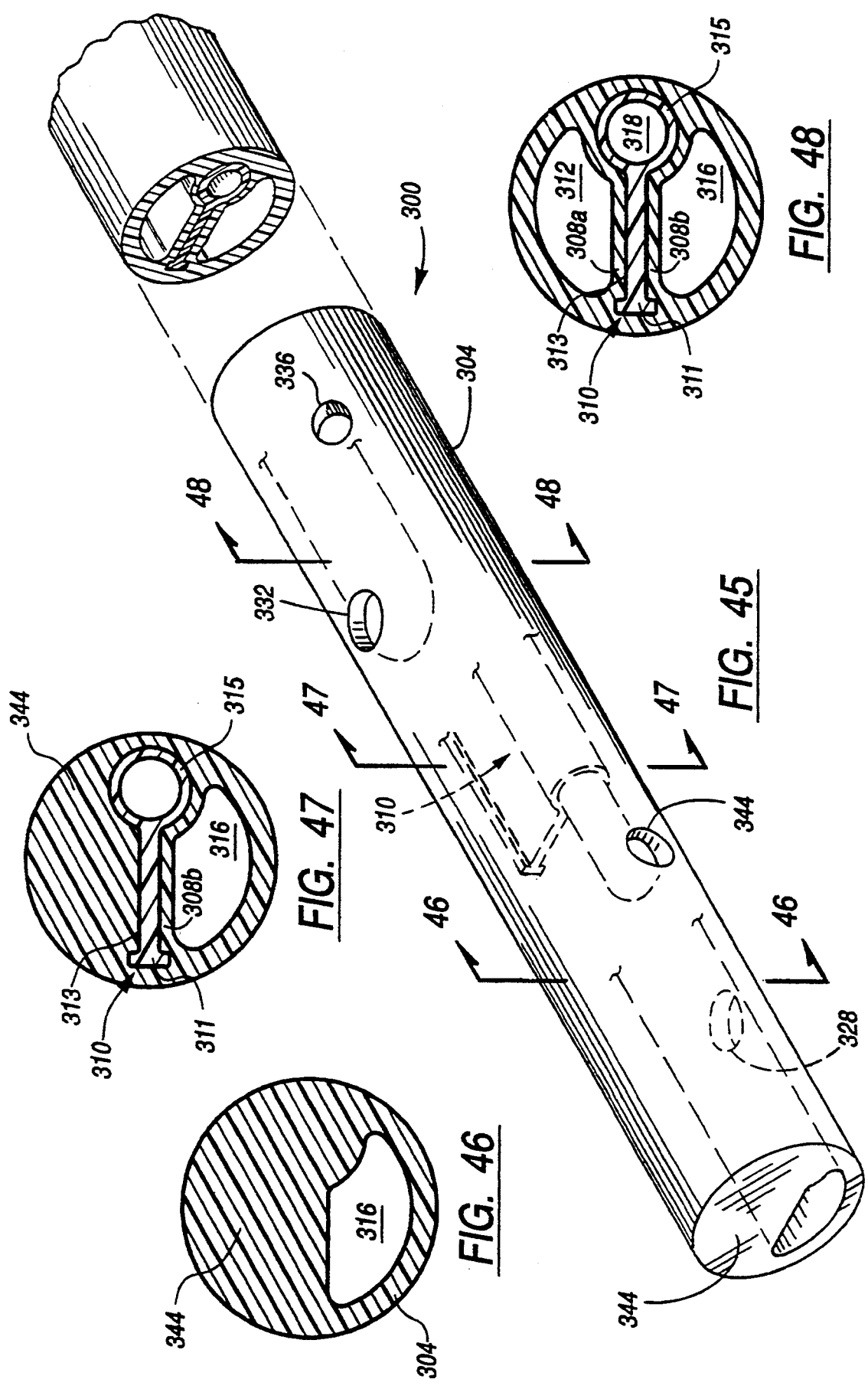

REINFORCED MULTIPLE-LUMEN CATHETER AND APPARATUS AND METHOD FOR MAKING THE SAME

REFERENCE TO RELATED APPLICATION

The present application is a continuation-in-part of U.S. application Ser. No. 07/903,896 filed Jun. 25, 1992 (now abandoned), and U.S. application Ser. No. 07/776,873 filed Oct. 16, 1991 (now issued as U.S. Pat. No. 5,221,244), which is a continuation of U.S. application Ser. No. 07/463,285 filed Jan. 10, 1990 (now abandoned).

FIELD OF THE INVENTION

The present invention relates generally to multiple-lumen catheters for use in medical applications such as hemodialysis where fluids must flow simultaneously to and from a patient. In particular, the present invention relates to multiple-lumen catheters which are constructed to avoid deformation or collapse of one or more of the lumens. In addition, the invention relates to an apparatus and method for making multiple-lumen catheters using a co-extrusion die. The invention is also particularly concerned with a multiple-lumen catheter which permits the catheter to be positioned in convenient anatomical sites during the periods between successive extracorporeal blood treatments to avoid patient discomfort and accidental displacement of the catheter, and to facilitate sterile attachment of the catheter to the patient during such periods.

BACKGROUND OF THE INVENTION

Dual-lumen catheters have come into widespread use for extracorporeal blood purification procedures such as hemodialysis. Blood is withdrawn from the patient through one of the lumens of the catheter and supplied to a hemodialysis unit where the blood is purified, and the resulting purified blood is then returned to the patient through the other lumen of the catheter. Examples of such catheters are shown in U.S. Pat. Nos. 4,134,402; 4,583,968; 4,568,329 and 4,692,141.

At the present time most dual-lumen catheters used for hemodialysis are made of either polyurethane or silicone rubber. The polyurethane catheters are sufficiently rigid that they can be introduced into a patient's vein percutaneously, without surgery, but such catheters tend to be incompatible with by the human body when left in place for long periods of time (e.g., a month or more). The silicone catheters can be left in place indefinitely without allergic reactions or traumatic problems in most patients, but the initial insertion of such catheters usually requires surgical intervention; the soft, pliable, elastic properties of the silicone which contribute to its compatibility with the human body are the same properties that make it difficult or impossible to insert such catheters percutaneously into a patient's vein.

SUMMARY OF THE INVENTION

It is a primary object of this invention to provide an improved multiple-lumen catheter which can be made of silicone or other relatively soft, elastic materials which are unlikely to be rejected by the body, and thus can be used for long-term applications, and yet can be inserted into a patient without surgery.

It is another important object of this invention to provide an improved multiple-lumen catheter which can be made of silicone, and yet can be inserted with the use of a needle, guide wire and peel-apart sheath, i.e., without surgical intervention.

A further object of this invention is to provide an improved multiple-lumen catheter which can be adapted for long-term use in femoral veins with little or no danger of infection. In this connection, a related object of the invention is to provide such an improved catheter which permits the access site for the catheter to be located above the thighs of the patient.

A still further object of this invention is to provide an improved apparatus and method for making a multiple-lumen catheter.

Another object of this invention is to provide an improved multiple-lumen catheter-connecting system which permits the catheter to remain relatively stable during the entire time the catheter remains inserted in the patient, even during long-term use of the catheter extending over numerous extracorporeal blood treatments. In this connection, related objects of the invention are to provide such a catheter-connecting system which significantly improves the comfort level of the patient in whom the catheter is inserted, and which greatly reduces the risk of venous damage.

In accordance with the present invention, the foregoing objectives are realized by providing a multiple-lumen catheter, comprising an elongated cylindrical tube made of a soft elastic material and having an internal septum extending along the length thereof to form a pair of longitudinal lumens; and a reinforcing member extending along the full length of at least one of the lumens for transmitting forces applied to the proximal end of the tube to the distal end of the tube. In a preferred embodiment, the reinforcing member is I-shaped, is embedded in the septum, and is made of a material which is substantially stiffer than the material of the tube so that the catheter can be advanced against a resistance by the application of force to the proximal end of the catheter. The reinforcing member also avoids deformation and/or collapse of one or more of the lumens when a pressure gradient exists across the septum.

This invention also provides an apparatus for making a multiple-lumen catheter, comprising a co-extrusion die having a pair of mandrels extending along a portion of the length of the die, and an extruder and rollers for simultaneously feeding different resins through the co-extrusion die. In a preferred embodiment, each of the mandrels has a D-shaped transverse cross-section such that each of the mandrels has a flat side extending along the length thereof. The flat side of one of the mandrels is positioned opposite to the flat side of the other of the mandrels, the flat faces being separated to form a gap between them. The extruder feeds a soft, elastic first resin into the co-extrusion die, and the rollers simultaneously feed a substantially stiffer second resin into the gap between the mandrels.

In addition, this invention provides a method for making a multiple-lumen catheter, the method comprising the steps of: (1) forming an elongated cylindrical tube with an internal septum extending along the length thereof to form a pair of longitudinal lumens; (2) while the elongated cylindrical tube is being formed, a reinforcing member is arranged within the septum; and (3) solidifying the elongated cylindrical tube.

Furthermore, this invention provides a multiple-lumen catheter assembly, comprising a multiple-lumen catheter having a distal end and a proximal end; a hub having one end fastened to the proximal end of the catheter; and extension tubes each having one end fastened to the opposite end of the hub from the catheter. The distal end of the catheter is bent back toward the extension tubes to form a bend having a predetermined shape. The bend is adapted to flex and deform from the predetermined shape in response to an external force and is adapted to return to the predetermined shape in response to removal of the external force.

BRIEF DESCRIPTION OF THE DRAWINGS

Other objects and advantages of the invention will become apparent upon reading the following detailed description and upon reference to the accompanying drawings, in which:

FIG. 2 is an enlarged longitudinal section taken along a diameter of the distal portion of the catheter of FIG. 1, perpendicular to the septum inside the catheter, as generally illustrated by line 2—2 in FIG. 1;

FIG. 3 is an end elevation taken at the distal end of the catheter portion shown in FIG. 2, as illustrated by line 3—3 in FIG. 2;

FIG. 4 is a section taken generally along line 4—4 in FIG. 2;

FIG. 5 is a section taken generally along line 5—5 in FIG. 2;

FIG. 6 is a section taken generally along line 6—6 in FIG. 2;

FIG. 8 is a section taken generally along line 8—8 in FIG. 7;

FIG. 9 is a section taken generally along line 9—9 in FIG. 7;

FIG. 10 is a section taken generally along line 10—10 in FIG. 7;

FIG. 14 is an enlarged longitudinal section taken generally along line 14—14 in FIG. 13;

FIG. 15 is an end elevation taken at the distal end of the catheter portion shown in FIG. 14, as illustrated by line 15—15 in FIG. 14;

FIG. 16 is a section taken generally along line 16—16 in FIG. 14;

FIG. 17 is a section taken generally along line 17—17 in FIG. 14;

FIG. 18 is a section taken generally along line 18—18 in FIG. 14;

FIG. 19 is a longitudinal section similar to FIG. 2 but showing a modified embodiment of the invention;

FIG. 20 is an end elevation taken at the distal end of the catheter portion shown in FIG. 19, as illustrated by line 20—20 in FIG. 19;

FIG. 21 is a section taken generally along line 21—21 in FIG. 19;

FIG. 22 is a section taken generally along line 22—22 in FIG. 19;

FIG. 23 is a section taken generally along line 23—23 in FIG. 19;

FIG. 24 is a longitudinal section similar to FIG. 2 but showing another modified embodiment of the invention;

FIG. 25 is an end elevation taken at the distal end of the catheter portion shown in FIG. 24, as illustrated by line 25—25 in FIG. 24;

FIG. 26 is a section taken generally along line 26—26 in FIG. 24;

FIG. 27 is a section taken generally along line 27—27 in FIG. 24;

FIG. 28 is a section taken generally along line 28—28 in FIG. 24;

FIG. 29 is a longitudinal section similar to FIG. 2 but showing a further modified embodiment of the invention;

FIG. 30 is an end elevation taken at the distal end of the catheter portion shown in FIG. 29, as illustrated by line 30—30 in FIG. 29;

FIG. 31 is a section taken generally along line 31—31 in FIG. 29;

FIG. 32 is a section taken generally along line 32—32 in FIG. 29;

FIG. 33 is a section taken generally along line 33—33 in FIG. 29:

FIG. 37 is an enlarged perspective view of the distal portion of the catheter embodying the present invention, the catheter having a conical tip;

FIG. 38 is an enlarged section taken generally along line 38—38 in FIG. 37;

FIG. 39 is an enlarged section taken generally along line 39—39 in FIG. 37;

FIG. 40 is an enlarged section taken generally along line 40—40 in FIG. 37;

FIG. 41 is an enlarged perspective view of the distal portion of a modified catheter embodying the invention, the catheter having a sliced tip;

FIG. 42 is an enlarged section taken generally along line 42—42 in FIG. 41;

FIG. 43 is an enlarged section taken generally along line 43—43 in FIG. 41;

FIG. 44 is an enlarged section taken generally along line 44—44 in FIG. 41;

FIG. 45 is an enlarged perspective view of the distal portion of a modified catheter embodying the invention, the catheter having a blocked tip;

FIG. 46 is an enlarged section taken generally along line 46—46 in FIG. 45;

FIG. 47 is an enlarged section taken generally along line 47—47 in FIG. 45;

FIG. 48 is an enlarged section taken generally along line 48—48 in FIG. 45;

Figure 1:
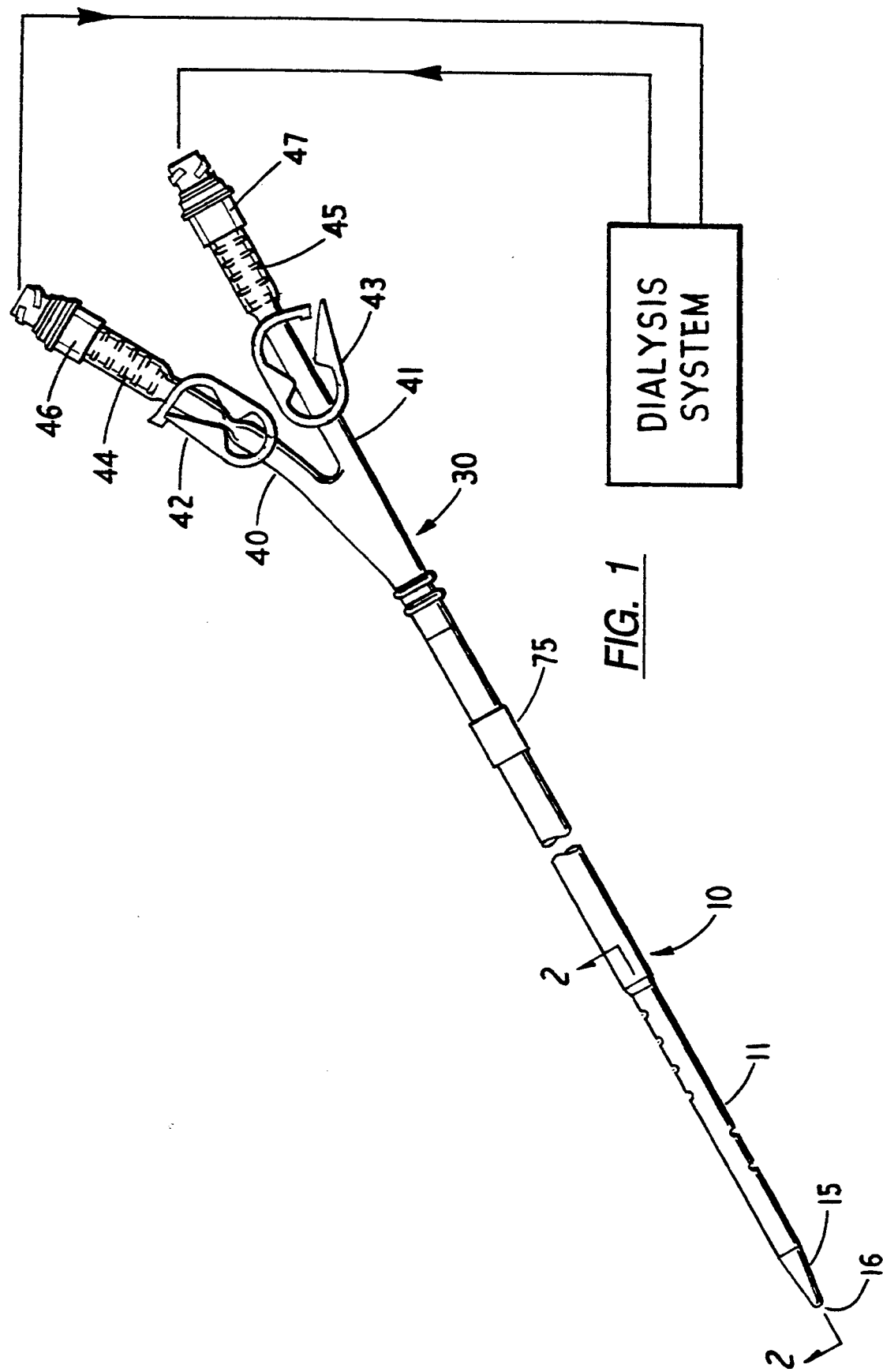
FIG. 1 is a perspective view of a dual-lumen hemodialysis catheter assembly embodying the present invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Turning now to the drawings and referring first to FIGS. 1-6, there is shown a dual-lumen hemodialysis catheter 10 of the general type described in Mahurkar U.S. Pat. No. 4,583,968, issued Apr. 22, 1986, for "Smooth Bore Double Lumen Catheter". This catheter 10 has a cylindrical body portion 11 made of silicone. The body portion 11 is hollow except for a flat, longitudinal, diametral septum 12 which divides the interior of the hollow cylinder into two parallel lumens 13 and 14, each having a D-shaped cross section (FIGS. 2 and 6). As illustrated by the arrows in FIG. 2, the lumen 13 is the blood-intake lumen, and the lumen 14 is the blood-return lumen.

At the distal end of the catheter, the exterior surface of the cylinder 11 merges into a smoothly tapered conical tip 15. On the inside, the blood return lumen 14 extends longitudinally all the way through the tip 15, bending slightly as it passes through the tip so that it opens at 16 near the center of the distal end of the conical tip, as can be seen in FIGS. 2 and 3. Within the tip 15, the cross-sectional shape of the lumen 14 gradually changes from D-shaped at the proximal end of the tip 15 (see FIG. 4) to circular at the distal end of the tip (see FIG. 3). The transition from D to circular is illustrated by the broken lines in FIG. 3.

In addition to the opening 16 at the distal end of the blood-return lumen 14, a pair of apertures 17 and 18 are formed in the side wall of the return lumen. These apertures 17 and 18, which are spaced longitudinally away from the distal opening 16 toward the proximal end of the catheter, ensure the flow of blood through the return lumen 14 even in situations where the distal opening 16 might become wholly or partially blocked. The area of the apertures 16, 17 and 18 is preferably at least equal to the transverse cross-sectional area of the return lumen 14.

In order to provide a longitudinal spacing between the distal openings of the two lumens 13 and 14, the blood-intake lumen 13 is terminated at an opening 21 in the side wall of the catheter. Additional openings 22–24 spaced longitudinally from the opening 21 permit blood to enter the lumen 13 freely without excessive vacuum in the event of a blockage of the opening 21 against the wall of the vein into which the catheter 10 is inserted.

Figure 7:
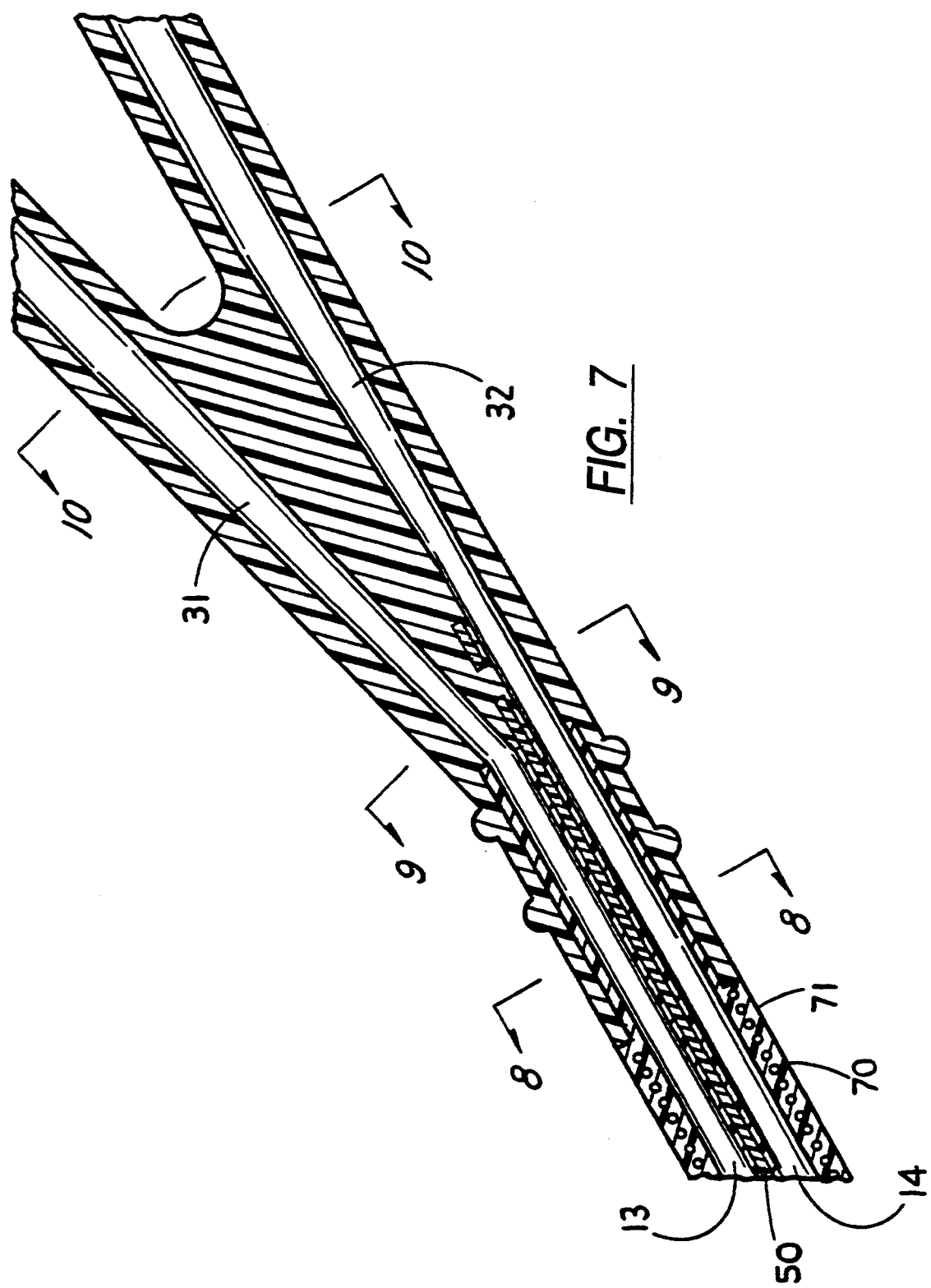
FIG. 7 is an enlarged horizontal section taken through the center of the y-shaped hub of the catheter of FIG. 1.

At the proximal end of the catheter 10, the two D-shaped lumens 13 and 14 open into a Y-shaped connector or hub 30 which forms two internal passageways 31 and 32 (see FIGS. 7-10) communicating with the proximal ends of the catheter lumens. As can be seen in FIGS. 7 and 9, the distal ends of the hub passageways 31 and 32 are D-shaped so that they form extensions of the catheter lumens 13 and 14, respectively. The passageways 31 and 32 diverge from each other and assume a circular cross section (see FIG. 10) as they extend toward the proximal end of the hub, and they also increase in cross-sectional area, as can be seen in FIGS. 7 and 10. The hub 30 is preferably molded in place on the end of the catheter, using mold inserts to form the hub passageways 31 and 32. Alternatively, the walls of the catheter lumens may be expanded at the proximal end of the catheter to fit over the corresponding portions of a preformed hub 30 with the inside walls of the catheter lumens being bonded to the mating walls of the hub 30.

To facilitate connection of the catheter hub 30 to the conventional tubes leading to a dialysis unit, and also to accommodate a pair of clamps for opening and closing the blood intake and return passageways, the hub 30 forms a pair of extension tubes 40 and 41 (FIG. 1). These extension tubes 40 and 41 are long enough to receive a pair of conventional clamps 42 and 43 for opening and closing the respective tubes. The extension tubes 40 and 41 are relatively soft and flexible, so that they can be easily manipulated and also easily closed by the pressure of the clamps 42 and 43. The clamps 42 and 43 serve as on-off valves for controlling the flow of blood between the catheter and the dialysis unit. At the proximal end of the hub 30, the hub passageways 31 and 32 open onto a pair of ferrules 44 and 45 formed as integral parts of luer connectors 46 and 47. The luer connectors serve as coupling means for coupling the proximal ends of the extension tubes to the flexible tubes leading to the extracorporeal blood treatment unit.

In accordance with one aspect of the present invention, a reinforcing member is embedded in the septum 12 and extends along the full length of the intake lumen 13. The reinforcing member is made of a material which is substantially stiffer than the silicone used to form the main body of the catheter, so that the catheter can be advanced against a resistance by the application of force to the proximal end of the catheter. In the illustrative embodiment of FIGS. 1-6, the reinforcing member is in the form of a flat polymeric strip 50 inserted longitudinally within a hollow septum 12.

The reinforcing strip 50 is made of a material that is stiff enough to transmit longitudinally applied forces from the proximal end of the catheter to the conical tip at the distal end of the catheter so that the catheter can be readily inserted into a patient percutaneously, i.e., without surgical intervention. One suitable material for the reinforcing strip is nylon, which provides the requisite degree of stiffness in a strip 0.135 inch wide and 0.012 inch thick. A preferred type of nylon is Nylon 1000, manufactured by Hoechst Celanese Corporation, Short Hills, N.J.

With the reinforcing strip, a silicone catheter can be easily inserted through a peel-apart sheath. Such a sheath is typically used after a guide wire has been introduced into a patient's vein by use of an access needle. The puncture formed by the needle is subsequently dilated by a smooth plastic tip on the end of a dilator telescoped through the pull-apart sheath and inserted a short distance into the vein. The dilator is then removed, the catheter is inserted through the sheath, and finally the sheath is removed by stripping it apart along two longitudinal tear lines.

Without the reinforcing member provided by this invention, attempts to insert a silicone catheter by the technique described above have usually resulted in radial expansion of the catheter at the entry to the sheath, due to the frictional resistance of the silicone surface engaging the inside wall of the sheath. Rather than causing the catheter to slide through the sheath, the applied insertion force resulted in expansion of the soft, elastic silicone material of the catheter body against the proximal end of the sheath, thereby preventing the catheter from sliding through the sheath.

With the present invention, however, the insertion force applied to the proximal end of the catheter is transmitted by the reinforcing member to the tip of the catheter, thereby "pulling" the catheter through the sheath. That is, the relatively stiff reinforcing member provides the catheter with sufficient column strength for easy insertion through the sheath. Although presently available materials that have the stiffness needed in the reinforcing material are not suitable for long-term implantation in the human body because of incompatibility problems such as localized allergic reactions, the present invention enables the reinforcing material to be isolated from the body. Thus, in the embodiment of FIG. 1, for example, the nylon reinforcing material is surrounded by the silicone material of the hollow septum. Therefore, it is only the silicone material that comes into contact with internal body tissues or fluids.

In addition, the reinforcing member prevents collapse of one of the lumens due to the pressure differential that normally exists across the septum of a dual-lumen catheter while it is being used to withdraw blood under a negative pressure in one lumen and to return blood under a positive pressure in the other lumen. With a silicone catheter, it is possible for the septum and the outside wall of the negative-pressure lumen to collapse together, thereby closing that lumen. The reinforcing strip, however, provides sufficient rigidity to the septum to prevent such collapsing of the negative-pressure lumen. Even when the outer wall of the lumen is not reinforced, the curvature of that wall normally prevents it from being collapsed against the septum as long as the septum itself cannot be distorted substantially toward the outer wall.

In the particular embodiment illustrated in FIGS. 1–6, the catheter tip 15 is molded as a unitary part of the catheter tube. This is accomplished by placing a tip mold around the distal end of the tube which forms the two D-shaped lumens, with the reinforcing strip in place and with mold inserts in place for forming the end of the intake lumen 13 and the extension of the return lumen 14 through the tip. As can be seen in FIGS. 2 and 4, the end portion of the reinforcing strip is preferably provided with a plurality of holes 51, 52 and 53 so that during the molding of the tip the molten silicone flows through the holes in the reinforcing strip (the entire distal end portion of the tube within the tip-forming mold is normally melted in this process). Then when the silicone is subsequently solidified, the reinforcing strip is locked firmly to the tip by the material that solidifies within the holes 51-53 of the strip. This interlocking of the reinforcing strip and the silicone holds the reinforcing strip securely in place, and ensures that the strip does not penetrate or separate through the relatively soft silicone tip during and after the insertion of the catheter.

At the proximal end of the catheter, the reinforcing strip 50 is similarly interlocked with the silicone that forms the hub 30. Thus, as can be seen in FIGS. 7 and 9, the proximal end of the strip 50 forms a hole 54 for receiving molten silicone during the in-situ molding of the hub 30. Then when the silicone solidifies, the strip 50 is securely interlocked with the hub 30.

To minimize kinking, the catheter of FIGS. 1–6 has a spiral 70 of relatively stiff material embedded in the cylindrical wall of the catheter along a substantial portion of the length of the catheter. The spiral 70 is preferably a thin metal wire wound helically around the extruded silicone tube, and then covered with a layer 71 of silicone so that the wire is not exposed to body tissue. The silicone is preferably applied as a liquid so that it flows around the spiral 70 and becomes a part of the silicone side walls of the catheter. If desired, a strong polymeric monofilament, e.g., nylon, may be used instead of the metal wire. The spiral 70 will always tend to retain its cylindrical shape, and thus also tends to hold the outer wall of the catheter in a cylindrical shape, thereby resisting kinking of the catheter. Consequently, the catheter can be bent, even at acute angles, without kinking. The use of such anti-kinking spirals in catheters is not new by itself, but the use of this feature in multiple-lumen silicone catheters such as those of the present invention leads to significant advantages in certain applications, as will be described in more detail below.

As shown in FIG. 1, a "Dacron" collar 75 is provided around the main body portion of the catheter to facilitate the growth of body tissues directly around the catheter where it enters the patient's body. The use of such a collar is well known in the catheter art.

Figure 12:
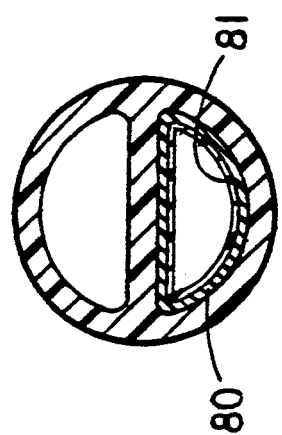
FIG. 12 is a section taken generally along line 12—12 in FIG. 11.
Figure 11:
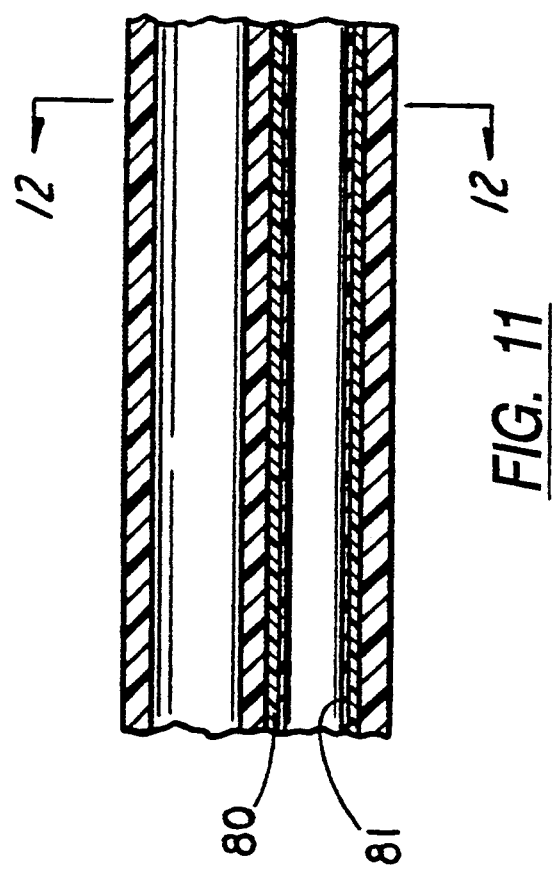
FIG. 11 is a fragmentary longitudinal section through the main body portion of a dual lumen catheter, normal to the septum, containing a modified reinforcing member.

FIGS. 11 and 12 illustrate a modified form of reinforcing member 80, which has a hollow D-shaped cross section, rather than the flat strip used in the embodiment of FIGS. 1–10. The D-shaped reinforcing member 80 is dimensioned to fit snugly within the intake lumen 13, with the distal end of the member 80 abutting the solid tip at the distal end of the lumen 13 (see FIG. 2). After the reinforcing member 80 has been inserted into the lumen 13, a thin layer 81 of silicone is formed on the inside walls of the member 80, e.g., by simply wicking a silicone liquid through the interior of the member 80 by capillary action.

If desired, the D-shaped reinforcing member 80 may be inserted into the intake lumen 13 only during insertion of the catheter into the patient. After the catheter is inserted, the reinforcing member 80 can be withdrawn from the catheter via the hub 30.

FIGS. 13–18 illustrate a catheter like the catheter of FIGS. 1–10 except that there is no reinforcing spiral around the outside wall of the catheter. This catheter is preferred for applications where kinking is not a problem, such as for implantation in the subclavian vein. The parts of the this catheter which are the same as those of the catheters of FIGS. 1–10 have been identified by the same reference numerals in FIGS. 13–18.

FIGS. 19–33 illustrate different configurations for the distal ends of catheters embodying this invention. Thus, the catheter of FIGS. 19–23 is made with a tapered conical tip 90 which is pre-molded and then inserted into the end of the extruded tube forming the two D-shaped lumens and the hollow septum. The reinforcing strip 50a in this embodiment is not apertured, but it extends slightly beyond the distal end of the cylindrical tube so as to fit into a mating slot formed in the pre-molded tip 90. The tip 90 also forms a D-shaped extension 91 which fits into the intake lumen and extends up to the edge of the first sidewall aperture, so as to form the terminus of the intake lumen. A shorter, hollow extension or "flash" 92 fits into the distal end of the return lumen, and is tapered to provide a smooth transition between the lumen of the cylindrical tube and the continuation of that lumen formed by the hollow tip. This pre-molded tip 90 is preferably made of silicone, and is bonded to the interior walls of the extruded tube by a silicone adhesive.

In the catheter of FIGS. 24–28, the intake lumen is terminated with an open end 100 by simply slicing off the distal portion of the lumen with a beveled cut. The return lumen continues all the way to the distal end of the tube, and retains the same D-shaped cross sectional configuration along its entire length. The reinforcing member 50b terminates in the region between the distal ends of the return lumen and the intake lumen, and the distal end portion of the hollow cavity formed by the septum is filled with a solid plug 101.

When the distal portion of the lumen is sliced off with a beveled cut, the unsliced extended lumen tends to curl due to the release of elastic forces on the sliced portion. The distal end is straightened by a thermoforming operation, in which the catheter is held in a straight position and heated by dry heat sufficient to alter the form of the nylon. This quantum of the heat does not affect the silicone in any way. Once the catheter cools, the distal end become straight.

In the catheter of FIGS. 29–33, the intake lumen is terminated by an insert 110 which fills the distal end portion of the intake lumen formed by the extruded tube, from the distal end of the tube to the edge of the first sidewall aperture. The return lumen and the reinforcing member are exactly the same as in the catheter of FIGS. 24–28 described above.

One particularly advantageous application for the kink-resistant catheters of this invention is an improved long-term implantation technique for the femoral vein. In contrast to the subclavian vein, the femoral vein is readily accessible through the thigh and is well removed from critical organs such as the lungs and heart. Nevertheless, the femoral vein has not been a popular access site for hemodialysis catheters because of the higher risk of infection below the inguinal canal. With the kink-resistant catheters provided by the present invention, however, the catheter can extend downwardly from a point above the inguinal ligament through a subcutaneous tunnel, and then bent upwardly for insertion into the femoral vein.

Figure 13:
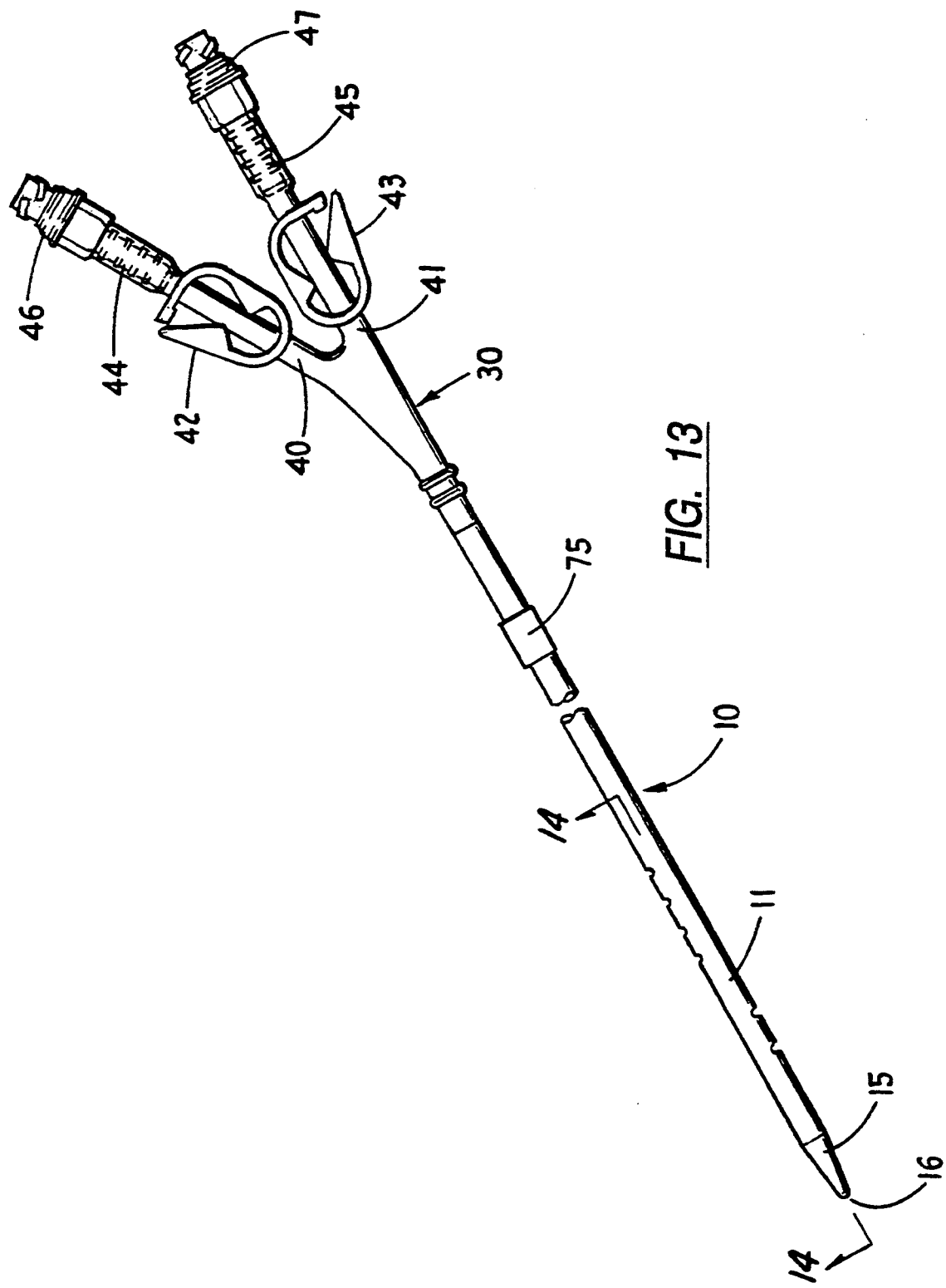
FIG. 13 is a perspective view of a modified dual-lumen hemodialysis catheter assembly embodying the invention.

One method of making the catheter of FIG. 13 is to extrude the main body portion of the catheter as a cylindrical tube having a hollow septum dividing the interior of the tube into two D-shaped lumens and a central cavity for receiving the reinforcing strip 50 (see FIG. 18). The extruded tube can be cut into the desired lengths for individual catheters. The strip 50 is then inserted into the central cavity, and the tip 15 and the hub 30 are formed on opposite ends of the tube by conventional techniques.

Figure 34:
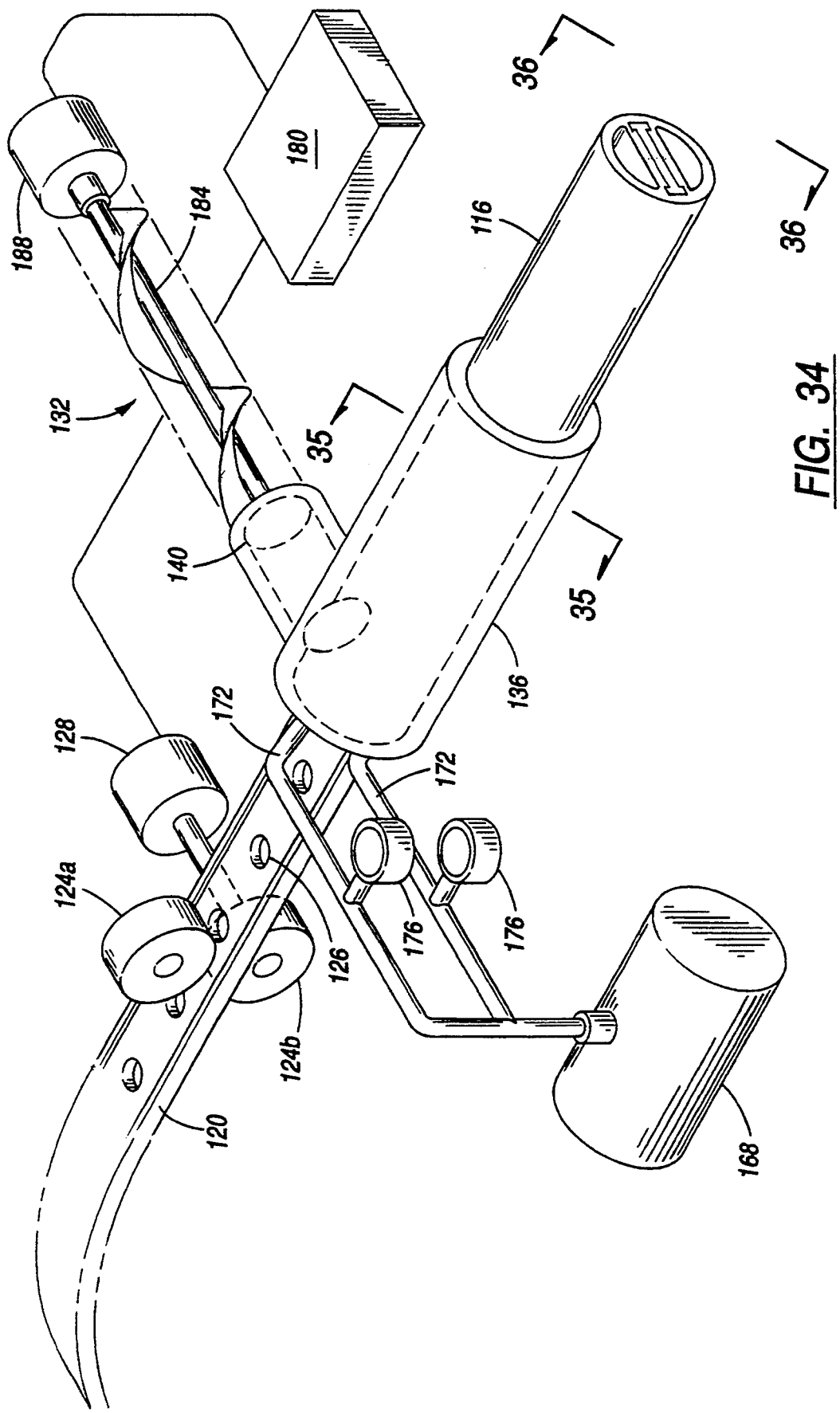
FIG. 34 is a perspective view of an apparatus for making a multiple-lumen catheter, the apparatus including a co-extrusion die.

Alternatively, FIG. 34 illustrates co-extrusion of a dual-lumen tube 116 with a continuous reinforcing strip 120 in the septum. The dual-lumen tube 116 is preferably made of silicone and the reinforcing strip 120 is made of nylon. The nylon strip 120 used in the co-extrusion process is supplied on a spool which feeds the nylon strip through rollers 124a,b driven by a motor 128. The motor drives the bottom roller 124b which, in turn, causes rotation of the top roller 124a when the nylon strip 120 passes therebetween. Alternatively, both rollers 124a, 124b are driven synchronously. To prepare the silicone for extrusion, the silicone is softened by milling it into sheets that are used for extrusion of dual-lumen catheters. While milling, an additive, barium sulfate, is added to the silicone to make the extrusion opaque to X-rays, which allows the catheter to be located in a human body. In addition, the silicone is provided with a vulcanizing agent, which is typically some form of organic peroxide, to maintain the final shape of the silicon tube 116 when it is heat cured.

Since silicone does not bond with thermoplastics, an intermediary adhesive that can bond with thermoplastics such as nylon as well as silicone is used to secure an indirect bond between silicone and nylon. To insure that the silicone tube 116 bonds to the nylon strip 120, the bonding surface of the nylon strip is first roughened with an abrasive, and later cleaned and degreased with acetone or CHROLOTHENE ®. When the bonding surface is dried, the surface is coated with a primer, such as SILASTIC ® S-2260 or 1200 RTV primer manufactured by Dow Corning Corporation, Saginow, Mich., by wiping, brushing, or spraying. As the solvent evaporates, the active ingredients in the prime coat hydrolyze by exposure to moisture in the air.

After coating the nylon strip with primer, an adhesive is applied to the nylon strip by brushing, spraying, or dipping the strip. The adhesive used in the preferred embodiment is SILASTIC ® Medical Adhesive Type A manufactured by Dow Corning Corporation, Saginow, Mich. This will eventually result in a thin coat of silicone elastomer on the strip, which is then preferably cured at room temperature for 72 hours at a relative humidity level between 20 and 60 percent. Allowing time for the adhesive to cure promotes a proper bond between the nylon strip 120 and the silicone tube 116 with which it will be co-extruded. Once the nylon strip is cured, it is re-spooled and prepared for the co-extrusion process.

Co-extrusion of the dual-lumen tube and the reinforcing strip is carried out by use of the rollers 124a,b for continuous nylon extrusion, a silicone extruder 132, and a co-extrusion die 136. The rollers 124a, b feed the nylon strip 120 into the co-extrusion die 136 while the silicone extruder 132 injects silicone into the die 136 at the input port 140. During the co-extrusion process, the nylon is fed to the co-extrusion die in solid form, while the silicone is fed to the die as softened milled sheets. To maintain the nylon in solid form, the temperature during the extrusion process does not exceed the melting point of the nylon. The minimum and maximum melting points of Nylon 1000 manufactured by Hoechst Celanese Corporation is between 510° F. and 550° F. Moreover, the temperature during the extrusion process is kept below 130° F. to prevent the silicone from scorching or losing its vulcanizing agents prematurely.

Figure 35:
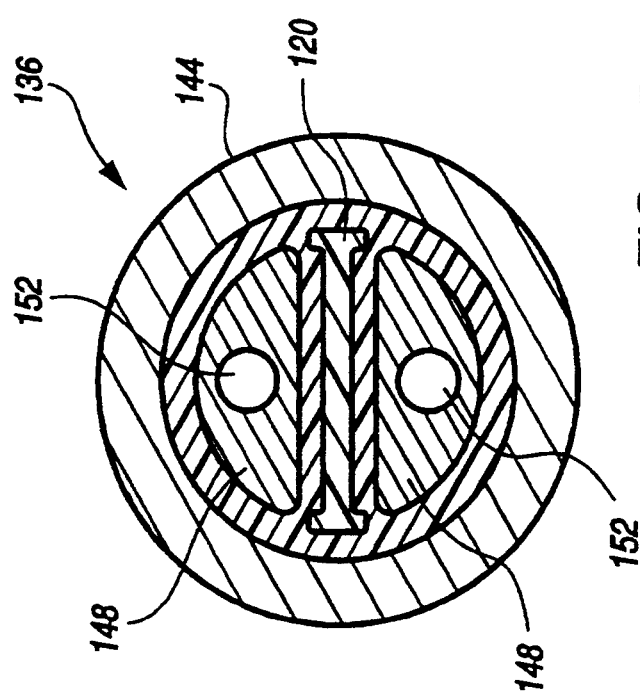
FIG. 35 is an enlarged section taken generally along line 35—35 in FIG. 34.

FIG. 35 illustrates the die cross-section near the output face of the die 136. Referring to FIG. 35 in connection with FIG. 34, the co-extrusion die 136 includes an outer casing 144 and a pair of D-shaped mandrels 148 with air channels 152 passing therethrough. The D-shaped mandrels 148 extend along a portion of the length of the die and are used to form two lumens 156 of the dual-lumen tube 116. The D-shaped mandrels 148 are oriented parallel to one another with their flat sides facing one another. The space between the flat sides of the mandrels forms a gap which receives the nylon strip 120 and silicone webs 160 on opposing sides of the nylon strip 120.

To make the dual-lumen tube 116 containing the strip 120, the nylon strip 20 and silicone are simultaneously injected into the co-extrusion die 136. In flowing through the co-extrusion die 136 adjacent to the mandrels 148, the silicone fills the circumferential space surrounding the mandrels 148 along with the gap between the mandrels 148 to form the dual-lumen tube 116 having the internal septum. The distance between the hemicircumference of the D-shaped mandrels 148 and the inner circumference of the circular die casing 144, as well as the extrusion pressure and the speed of the silicone flow, determine the wall thickness of the dual-lumen tube 116.

While the silicone is being fed into the co-extrusion die 136, the solid nylon strip 120 is directed into the gap between the mandrels 148 so that the nylon strip 120 traverses the gap with the silicone flowing on both sides of the nylon strip 120. The flow of silicone with the nylon strip 120 disposed therein creates the internal septum with a reinforcing member. The distance between the flat sides of the juxtaposed D-shaped mandrels 148 determines the thickness of the septum. Co-extrusion of the tube 116 and the nylon strip 120 allows the thickness of the two septum webs surrounding the reinforcing member to be thinner than the webs formed by extrusion of the tube without the strip (i.e., the strip being inserted afterward). One reason for this is that co-extrusion does not require that the two septum webs be self-supporting because the co-extruded strip provides support. Moreover, since the septum webs are co-extruded with the strip, the septum webs do not have to be of a thickness capable of withstanding the friction created by inserting the strip.

Figure 36:
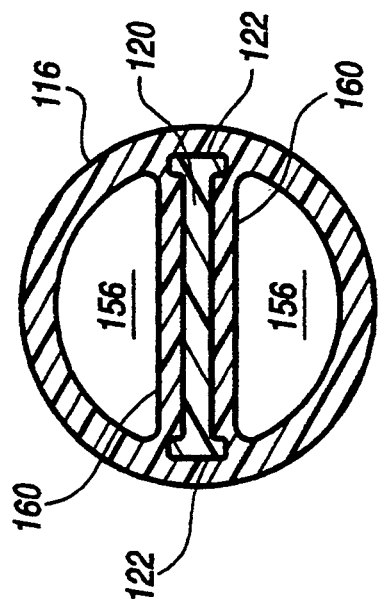
FIG. 36 is an enlarged section taken generally along line 36—36 in FIG. 35.

The mandrels 148 terminate within the co-extrusion die 136 at a predetermined length from the output face of the die 136. As the silicone-nylon extrudate flows past the termination point of the mandrels 148, the septum is maintained in the mid-line of the tubular extrusion by keeping the air pressure in each lumen identical. This is achieved by injecting air from a compressor source 168 into the air channels 152 of the mandrels 148 via air tubes 172. Although separate compressor sources could be used, employing a single compressor source insures that the air pressure through each air channel and associated lumen is identical. The air pressure in the air tubes 172 is measured by the guages 176. In addition to maintaining the septum in the mid-line of the tubular extrusion, the air flow through the newly formed lumens 156 prevents the lumens 156 from collapsing. FIG. 36 illustrates the extruded dual-lumen tube 116 with the nylon strip 120.

A control unit 180, coupled to both a motor 188 of the silicone extruder 132 and the motor 128, insures that the silicone from extruder 132 and the nylon strip 120 are fed into the co-extrusion die 136 at the same rate. The flow rate of silicone is determined primarily by the rotation rate of an extruder screw 184 driven by a motor 188, as well as the temperature of the silicone. The control unit 180 sets the rotation rate of the motor 128 driving the bottom roller 124b such that the nylon strip 120 is fed into the co-extrusion die 136 by the rollers 24a,b at the same speed as the silicone is fed into the die by the silicone extruder 132.

Several features of the present invention aid in securing the nylon strip 120 within the septum of the dual-lumen tube 116. First, as discussed previously, the nylon strip 120 is treated with adhesive to promote bonding between the strip 120 and the co-extruded silicone tube 116. In addition, as depicted in FIG. 36, the nylon strip 120 is provided with orthogonal side plates 122. The width of the strip 120 is preferably slightly greater than the inside diameter of the silicone tube 116 so that the side plates 122 extend slightly into the cylindrical walls of the tube 116. With the side plates 122, the cross-section of the reinforcing strip 120 resembles an I beam. The I beam further aids in anchoring the reinforcing nylon strip 120 in the septum and the circumferential wall of the dual-lumen tube 116. Furthermore, the nylon strip 120 is provided with a plurality of holes 126 so that during the co-extrusion the molten silicone flows through the holes 126 in the strip 120. When the silicone is subsequently solidified, the reinforcing strip 120 is locked firmly within the septem by the solidified silicone within the holes 126 of the strip 120.

After exiting from the co-extrusion die 136, the extruded dual-lumen tube 116 is cut into sections to form the tubing for separate dual-lumen catheters. These sections are then vulcanized and cured in an oven with circulating hot air at an appropriate temperature not exceeding the melting point of nylon. Curing the tubing stabilizes the silicone and attains the desired physical properties of the tubing.

FIGS. 37-48 illustrate different configurations for distal ends of catheters produced by the co-extrusion apparatus in FIG. 34. The catheter of FIGS. 37-40 is made with a tapered conical tip 220 and has an elongated cylindrical body portion 204 made of silicone. The body portion 204 is hollow except for a longitudinal, diametral septum 208 with a nylon reinforcing member 210 embedded therein. The septum 208 divides the interior of the hollow body portion 204 into two lumens 212 and 216. The lumens 212 and 216 are semi-cylindrical with D-shaped cross sections (FIG. 40) which occupy a major portion of the transverse cross-section of the interior of the cylindrical tube. The lumen 212 is the blood-intake lumen, and the lumen 216 is the blood-return lumen.

At the distal end of the catheter 200, the exterior surface of the body portion 204 merges into the smoothly tapered frusto-conical tip 220. On the inside, the blood return lumen 216 extends longitudinally all the way through the tip 220, bending slightly as it passes through the tip 220 so that it opens at 224 near the center of the distal end of the conical tip. Within the tip 220, the cross-sectional shape of the lumen 216 gradually changes from D-shaped at the proximal end of the tip 220 (see FIG. 37) to circular at the distal end of the tip 220 (see FIG. 6). The transition from D to circular is illustrated by the broken lines in FIG. 37.

The catheter tip 220 is preferably made of silicone and may be molded as a unitary part of the catheter tube. This is accomplished by placing a tip mold with a conically tapered cavity around the distal end of an extruded tube which forms the two lumens, with a pin in place for forming the extension of the return lumen 216 through the tip and a tapered silicone plug in place for forming the distal portion of the lumen 212. The silicone is injected in the heated mold and allowed to set. Once the silicone sets, it is cured by heat to obtain its final form. Alternatively, the tip 220 is pre-molded and bonded to the interior walls of the extruded body portion 204 by a silicone adhesive in the manner described in connection with FIGS. 19-23.

In addition to the opening 224 at the distal end of the blood-return lumen 216, one or more auxiliary apertures 228 are formed in the side wall of the lumen 216. The illustrated side aperture 228, which is spaced longitudinally away from the distal opening 224 toward the proximal end of the catheter, prevents pressure build-up and ensures the flow of blood through the return lumen 216 even in situations where the distal opening 224 might become wholly or partially blocked. The area of the apertures 224 and 228 is preferably at least equal to the transverse cross-sectional area of the return lumen 216.

In order to provide a longitudinal spacing between the distal openings of the two lumens 212 and 216, the blood-intake lumen 212 is terminated at an aperture 232 in the side wall of the catheter, spaced longitudinally away from the aperture 228. An auxiliary aperture 236 spaced longitudinally and radially from the aperture 232 permits blood to enter the lumen 212 freely without excessive vacuum even in the event of a blockage of the aperture 232 against the wall of the vein into which the catheter 200 is inserted.

In the catheter of FIGS. 41–44, the intake lumen 212 is terminated with open end 240 by simply slicing off a distal portion of the lumen with a beveled or right-angled cut. The return lumen 216 continues all the way to the distal end of the tube, and retains the same D-shaped cross-sectional configuration along its entire length. When the distal portion of the intake lumen 212 is sliced off, the distal portion of the return lumen 216 assumes a curled shape due to a release of elastic forces by the silicone. This curled shape is straightened by using dry heat to impart a reverse memory bend to the nylon strip. The combination of the elasticity of the silicone and the memory bend applied to the nylon straightens the distal portion of the catheter.

Not only does the catheter of FIGS. 45–48 illustrate a different configuration for the distal end of the catheter, but the catheter also includes three lumens instead of two. The triple-lumen catheter, designated by the reference numeral 300, has a cylindrical body portion 304 containing a septum. The two larger lumens 312 and 3 16 are substantially semi-cylindrical with generally D-shaped cross sections (FIG. 48). The lumen 312 is the blood-intake lumen, and the lumen 316 is the blood-return lumen. The smaller third lumen 318 is located at one diametral end of the septum, where the septum is bifurcated before it joins the cylindrical outer wall of the catheter. Thus, the lumen 318 is located between two adjacent corners of the generally D-shaped lumens 312 and 316. This third lumen 318 has a circular transverse cross-section and can be used for a variety of different purposes, such as injecting liquid medications into the patient, withdrawing blood samples from the patient, or measuring the pressure in the vein of the patient. Because the lumen 318 is located at the corners of the lumens 312 and 316, there is only a slight reduction in the liquid-handling capacity of the lumens 3 12 and 316. For example, the lumens 312 and 316 are still capable of delivering 250 ml/min. of blood with a pressure gradient of 100 mm. of mercury, as required in most dialysis systems. A small lumen located in the corners of the large lumens 312 and 316 does not significantly reduce the liquid flow rates in the large lumens because the corners are regions where boundary layers of zero or low velocity converge and form a stagnation zone. A small lumen located in these corners is well away from the regions of high fluid flow in the lumens 312 and 316.

Because the third lumen 318 provided by this invention does not significantly compromise the blood flow rates in the two large lumens, a single catheter may be used for both hemodialysis and to provide access to the central veins of the patient for intravenous infusions, withdrawal of blood samples, and monitoring of venous pressures. This preserves the peripheral veins of the patient for construction of arterio-venous fistula, which are used for chronic maintenance hemodialysis. The third lumen 3 18 also may be used for other purposes, such as for containing a removable stylus to add column strength during insertion of the catheter, or to receive a guide wire for use in replacing a blocked catheter.

The blood-intake lumen 312 communicates with the external environment via apertures 332 and 336, which are comparable to the apertures 232 and 236 in FIG. 37. The blood-return lumen 316 extends longitudinally all the way through the distal end of the catheter. An auxiliary aperture 328, comparable to the aperture 228 in FIGS. 37 and 41, is formed in the side wall of the lumen 316.

The small third lumen 318 terminates at an aperture 348 in the sidewall of the catheter. This aperture 348 is located approximately midway between the aperture 332 and the far distal end of the catheter in the longitudinal direction, and 90° away from the aperture 332 in the circumferential direction. The aperture 348 is also spaced proximally away from the aperture 328 in the longitudinal direction. Thus, liquids injected into a patient through the lumen 318 are injected downstream of the blood intake ports 332 and 336, and blood samples withdrawn through the lumen 318 are taken upstream of the port 328.

In the illustrated embodiment of FIG. 45, the intake lumen 312 is terminated by a solid portion 344 which extends from the distal end of the tube to the edges of the sidewall apertures 348 and 332. The catheter of FIGS. 45–48 is formed with a silicone body and nylon reinforcing member 310 which includes both an orthogonal side plate 311, a flat strip 3 13, and a narrow hollow cylinder 315. The flat strip 313 is located between the webs 308a and 308b, and the cylinder 315 lines the inside walls of the small lumen 318. The side plate 311 is partially located within the cylindrical body portion 304, and aids in securing the reinforcing member 310 within the septum 308.

The lumen 318 is not used to conduct blood except for withdrawal of samples for analysis, and is normally either filled with heparin anticoagulant solution or closed when it is not being used for intravenous infusions or pressure monitoring. Thus, exposure of the nylon reinforcing material on the inside walls of the lumen 318 will not normally cause the patient's body to react to the catheter during prolonged implacements of the catheter. The nylon reinforcing member 310 may be co-extruded with the silicone body of the catheter, or it may be formed separately and then inserted into the silicone body.

The catheters in FIGS. 37–48 may be constructed with either two or three lumens. Therefore, the dual-lumen catheter having a conical tip, shown in FIGS. 37–40, may be constructed with three lumens arranged as shown in FIGS. 45–48. Similarly, the dual-lumen catheter having a sliced tip, shown in FIGS. 41–44, may be constructed with three lumens arranged as shown in FIGS. 45–48. Finally, the triple-lumen catheter having a blocked tip, shown in FIGS. 45–48, may be constructed with two lumens arranged as shown in FIGS. 37–44.

Figure 49:
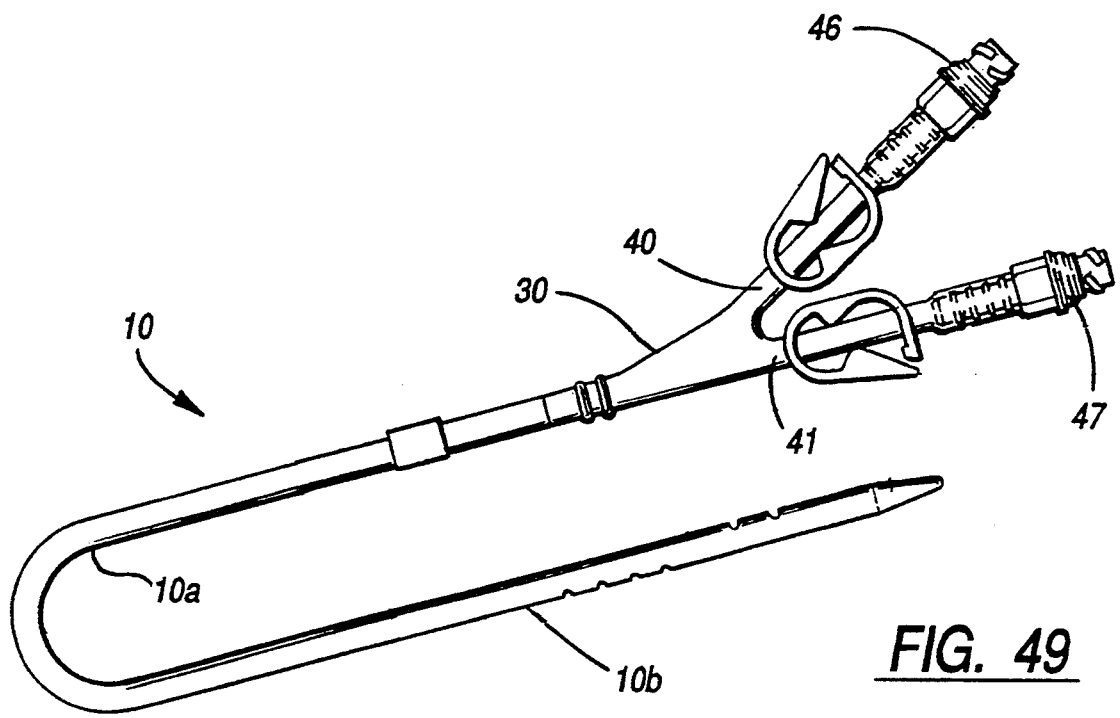
FIG. 49 is a perspective view of a dual-lumen catheter assembly with a U-bend in the catheter, embodying the present invention.
Figure 50:
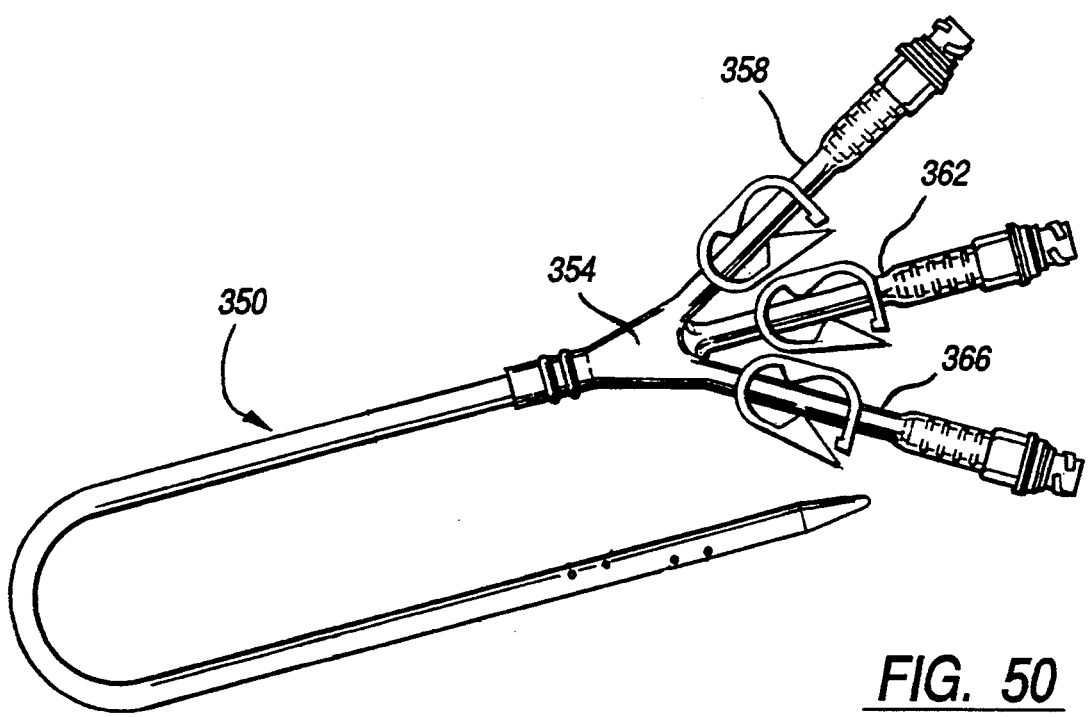
FIG. 50 is a perspective view of a triple-lumen catheter assembly with a U-bend in the catheter, embodying the present invention.

FIGS. 49–50 illustrate another important aspect of the present invention. As shown in the dual-lumen catheter assembly in FIG. 49, the proximal end of the dual-lumen catheter 10 is fastened to one end of the hub 30, and the opposite end of the hub 30 is fastened to a pair of flexible extension tubes 40 and 41. In accordance with the present invention, a U-shaped bend is imparted to the catheter assembly for the comfort of the patient. This U-shaped bend is achieved either by bending the extension tubes 40 and 41 or by bending the catheter 10; both provide identical comfort for a patient. During the curing operation following extrusion, the bend is imparted to the catheter simply by heating the catheter while holding it in the desired shape.

In the illustrated embodiment, the distal end of the catheter 10 is bent back toward the extension tubes 40 and 41, preferably extending along the sides of the hub 30 and the extension tubes 40 and 41. By providing the U-bend in the catheter 10, the auxiliary connecting elements attached to the proximal end of the catheter can be accommodated in a small area around the access site on the patient's body. Consequently, the entire connecting assembly for the catheter 10, including the luer fittings 46 and 47 on the proximal ends of the extension tubes 40 and 41, can be located on a protected portion of the patient's body. There are no projections to interfere with movements of the patient, or with the movement of people and articles around the patient. It is also easy for the patient to don and remove clothing, and normal clothing can be worn by the patient during interdialytic periods without any unsightly or embarrassing projecting portions of the catheter assembly.

Perhaps even more importantly, any forces exerted on the proximal ends of the extension tubes 40 and 41 tend to move the catheter 10 in a direction opposite that of the applied force. Thus, when pulling forces are exerted on the extension tubes by the long and relatively heavy tubes leading to the dialysis unit, for example, those forces tend to push the catheter into the patient to hold it in place rather than withdrawing the catheter. Consequently, the risk of accidental dislodgement of the catheter is greatly reduced, as is the risk of vein irritation and damage.

In the particular embodiment illustrated in FIG. 49, the U-bend in the catheter begins at a point 10a. The bend is exactly 180°, and terminates in a straight length of catheter tubing 10b. In addition, the U-bend is permanently formed in the catheter 10. That is, both the overall shape of the bend and the size of the interior passageway of the bend are set or "memorized" in the catheter so that the tube always returns to that configuration. The U-bend is still flexible but is substantially stiffer than the straight proximal end portion of the catheter 10, as a result of which any forces applied to the more flexible proximal end portion of the catheter 10 tend to simply pivot the proximal end portion about the relatively stiff bent portion. Consequently, the distal end of the catheter 10 is to a large extent isolated from bending moments applied to the proximal end portion of the catheter 10. This greatly reduces pivoting and tilting movement of the catheter 10 within the vein, thereby further reducing irritation of the vein walls and the attendant risk of venous damage.

FIG. 50 illustrates the same aspect of the present invention as FIG. 49, except that FIG. 50 shows a triple-lumen catheter assembly instead of a dual-lumen catheter assembly. In FIG. 50, the proximal end of a triple-lumen catheter 350 is fastened to one end of a hub 354, and the opposite end of the hub 354 is fastened to three flexible extension tubes 358, 362, and 366 (one per lumen). In accordance with the present invention, a U-shaped bend is imparted to the catheter 350 in the same manner as discussed in connection with FIG. 49.

The U-bend imparted to a catheter assembly, as in FIGS. 49–50, allows the catheter assembly to be nestled in a relatively small region around the access site on a patient's body, whether the access site be a subclavian vein, a jugular vein, a femoral vein, or some other location on the patient's body. A more in-depth description of the benefits associated with using a U-bend at these access sites and of how the catheter assembly is positioned at these access sites is given in U.S. Pat. No. 4,895,561 to Mahurkar, entitled "Dual-Lumen Catheter-Connecting System" and issued on Jan. 23, 1990, which is incorporated herein by reference.

Figure 51:
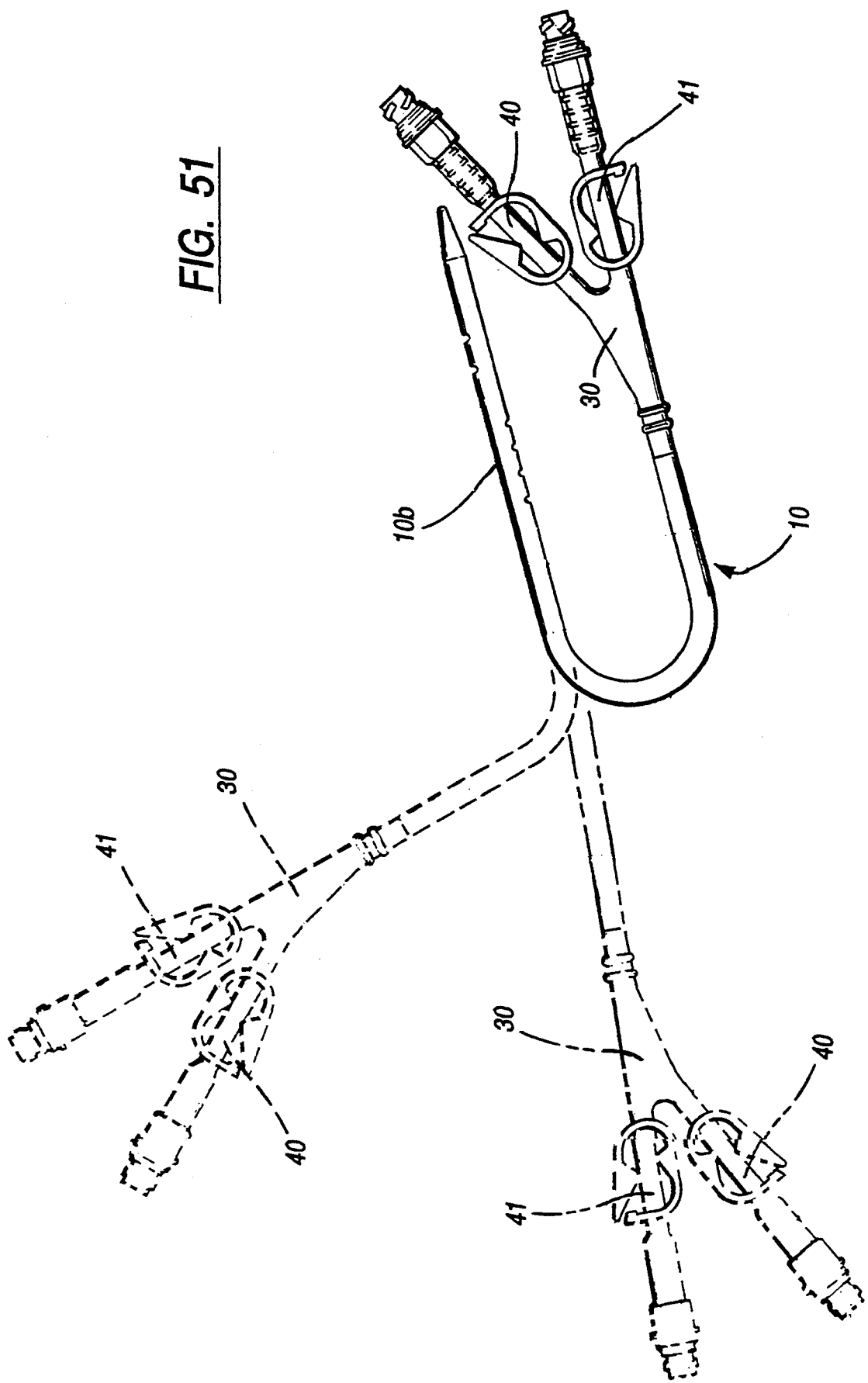
FIG. 51 is a side elevation of the catheter assembly in FIG. 49, illustrating the extensions tubes, the hub, and a proximal portion of the catheter in three different positions.

The relatively stiff U-bend also forms a fulcrum about which the extension tubes, the hub, and a proximal portion of the catheter can be turned to facilitate connection to a dialysis unit located anywhere within a 360° circle around the patient. This flexibility of the catheter assembly is illustrated in FIG. 51 for the dual-lumen catheter assembly in FIG. 49. FIG. 51 shows the extension tubes 40 and 41, the hub 30, and a proximal portion of the catheter 10 bent laterally to one side of the straight length of catheter tubing 10b in solid lines, to the other side in dashed lines, and in a direction away from the straight length of catheter tubing 10b in phantom lines.

While the present invention has been described with reference to one or more particular embodiment, those skilled in the art will recognize that many changes may be made thereto without departing from the spirit and scope of the present invention. For example, although the above co-extrusion method of making a dual-lumen catheter has been described with reference to nylon and silicone, other primary body-compatible materials for forming the dual-lumen tube and other highly rigid materials for forming the reinforcing strip can be used. Each of these embodiments and obvious variations thereof is contemplated as falling within the spirit and scope of the claimed invention, which is set forth in the following claims.

What is claimed is:

1. A method of making a multiple-lumen catheter using a co-extrusion die, comprising the steps of:
   forming an elongated cylindrical tube made of a soft, elastic material which is compatible with the human body, said tube having an internal septum extending along the length thereof to form at least a pair of longitudinal lumens;
   while the elongated cylindrical tube is being formed, arranging a diametral reinforcing member extending along the length of the tube and completely embedded within said soft compatible material of said tube and septum so that said reinforcing material is not exposed to blood passing through said lumens, the reinforcing member being made of a material which is substantially stiffer than the material of the tube; and
   solidifying the tube.

2. The method of claim 1, further comprising the step of curing the tube.

3. The method of claim 1, further comprising the step of cutting the tube into individual multiple-lumen catheters.

4. The method of claim 3, further comprising the step of molding a tip directly onto an end of each of the individual multiple-lumen catheters.

5. The method of claim 3, further comprising the step of preforming a conical tip and bonding the tip to the end of each of the individual multiple-lumen catheters.

6. The method of claim 3, further comprising the step of slicing off a distal portion of one of the lumens of each of the individual multiple-lumen catheters with a beveled cut so as to form a sliced tip.

7. The method of claim 3, further comprising the step of blocking off one of the lumens short of the distal end of each of the individual multiple-lumen catheters.

8. The method of claim 3, further comprising the step of connecting a hub with a plurality of extension tubes to the proximal end of each of the individual multiple-lumen catheters, a separate extension tube being in fluid communication with each of the lumens.

9. The method of claim 3, further comprising the step of curing each of the individual multiple-lumen catheters and imparting a generally U-shaped bend to each of the individual multiple-lumen catheters during the curing.

10. The method of claim 1, further comprising the step of applying an adhesive to the material used for making the reinforcing member prior to forming the tube.

11. The method of claim 1, wherein the step of arranging the reinforcing member inside the tube and extending along the length of the tube includes interlocking the reinforcing member and the tube.

12. The method of claim 3, further comprising the step of terminating a first lumen of each of the individual multiple-lumen catheters at a distal aperture at the distal end of each of the individual multiple-lumen catheters, and terminating a second lumen at a distal aperture in the side wall of the tube which is longitudinally spaced from the distal end of each of the individual multiple-lumen catheters.

13. The method of claim 12, further comprising the step of providing the first lumen with an auxiliary aperture in the side wall of the tube of each of the individual multiple-lumen catheters, the auxiliary aperture being longitudinally spaced from the distal aperture in the first lumen.

14. The method of claim 12, further comprising the step of providing the second lumen with an auxiliary aperture in the side wall of the tube of each of the individual multiple-lumen catheters, the auxiliary aperture being spaced longitudinally and radially away from the distal aperture in the second lumen.

15. The method of claim 1, further comprising the step of providing the reinforcing member with a plurality of spaced apertures located along the length of the reinforcing member.

16. The method of claim 1, wherein the reinforcing member is arranged within the internal septum.

17. The method of claim 1, further including the step of providing the reinforcing member in the form of a flat strip prior to the step of arranging the reinforcing member along the length of the tube.

18. The method of claim 17, wherein the step of providing the reinforcing member in the form of a flat strip includes providing the reinforcing member in the form of a flat strip with orthogonal side plates.

19. A method of making a multiple-lumen catheter using a co-extrusion die, comprising the steps of:

forming an elongated cylindrical tube made of a soft, elastic material which is compatible with the human body, said tube having an internal septum extending along the length thereof to form at least a pair of longitudinal lumens;

while the elongated cylindrical tube is being formed, arranging a diametral reinforcing member such that the reinforcing member is completely embedded within said soft compatible material of said tube and septum so that said reinforcing material is not exposed to blood passing through said lumens, the reinforcing member being a flat strip and being made of a material which is substantially stiffer than the material of the tube; and solidifying the tube.

* * * * *